(12) United States Patent
Sherman et al.

(10) Patent No.: US 7,229,810 B2
(45) Date of Patent: Jun. 12, 2007

(54) POLYMER CONJUGATES OF PROTEINASES

(75) Inventors: Merry R. Sherman, San Carlos, CA (US); Alexa L. Martinez, San Jose, CA (US); Shyam S. Bhaskaran, New York, NY (US); L. David Williams, Fremont, CA (US); Mark G. P. Saifer, San Carlos, CA (US); John A. French, Santa Cruz, CA (US)

(73) Assignee: Mountain View Pharmaceuticals, Inc., Menlo Park, CA (US)

( * ) Notice: Subject to any disclaimer, the term of this patent is extended or adjusted under 35 U.S.C. 154(b) by 388 days.

(21) Appl. No.: 10/183,607

(22) Filed: Jun. 28, 2002

(65) Prior Publication Data

US 2003/0012777 A1 Jan. 16, 2003

Related U.S. Application Data

(63) Continuation-in-part of application No. 10/103,128, filed on Mar. 22, 2002, now abandoned, which is a continuation-in-part of application No. 09/894,071, filed on Jun. 28, 2001, now abandoned.

(51) Int. Cl.
*C12N 9/96* (2006.01)
*C12N 9/56* (2006.01)
(52) U.S. Cl. ...................... 435/188; 435/222
(58) Field of Classification Search .......... 435/188, 435/222
See application file for complete search history.

(56) References Cited

U.S. PATENT DOCUMENTS

| | | | |
|---|---|---|---|
| 4,002,531 A | 1/1977 | Royer | |
| 4,179,337 A | 12/1979 | Davis et al. | |
| 4,609,546 A | 9/1986 | Hiratani | |
| 4,683,195 A | 7/1987 | Mullis et al. | |
| 4,683,202 A | 7/1987 | Mullis | |
| 4,962,020 A | 10/1990 | Tabor et al. | |
| 5,006,333 A | 4/1991 | Saifer et al. | |
| 5,080,891 A | 1/1992 | Saifer et al. | |
| 5,093,531 A | 3/1992 | Sano et al. | |
| 5,246,849 A | 9/1993 | Bryan et al. | |
| 5,252,714 A | 10/1993 | Harris et al. | |
| 5,278,062 A | 1/1994 | Samal et al. | |
| 5,283,317 A | 2/1994 | Saifer et al. | |
| 5,321,095 A * | 6/1994 | Greenwald | 525/404 |
| 5,409,818 A | 4/1995 | Davey et al. | |
| 5,455,166 A | 10/1995 | Walker | |
| 5,468,478 A | 11/1995 | Saifer et al. | |
| 5,476,653 A | 12/1995 | Pitt et al. | |
| 5,482,996 A * | 1/1996 | Russell et al. | 525/54.1 |
| 5,498,523 A | 3/1996 | Tabor et al. | |
| 5,672,662 A | 9/1997 | Harris et al. | |
| 5,766,897 A | 6/1998 | Braxton | |
| 5,824,784 A * | 10/1998 | Kinstler et al. | 530/399 |
| 5,837,517 A | 11/1998 | Sierkstra et al. | |
| 5,847,110 A * | 12/1998 | Dragsten et al. | 536/124 |
| 5,856,451 A | 1/1999 | Olsen et al. | |
| 5,981,718 A | 11/1999 | Olsen et al. | |
| 6,114,509 A | 9/2000 | Olsen et al. | |
| 6,190,900 B1 | 2/2001 | Sierkstra et al. | |
| 6,201,110 B1 | 3/2001 | Olsen et al. | |
| 6,214,966 B1 | 4/2001 | Harris | |
| 6,245,901 B1 | 6/2001 | von der Osten et al. | 530/402 |
| 6,300,116 B1 | 10/2001 | von der Osten et al. | |
| 6,416,756 B1 * | 7/2002 | Olsen et al. | 424/94.63 |
| 6,495,136 B1 * | 12/2002 | Weisgerber et al. | 424/94.64 |
| 6,623,950 B1 * | 9/2003 | von der Osten et al. | 435/220 |
| 6,964,764 B2 * | 11/2005 | Zimmerman et al. | 424/94.64 |

FOREIGN PATENT DOCUMENTS

| | | |
|---|---|---|
| EP | 0 215 662 A1 | 3/1987 |
| EP | 0 329 822 B1 | 8/1989 |
| EP | 0 471 125 A1 | 2/1992 |
| EP | 0 534 858 B1 | 3/1993 |
| EP | 0 684 315 A1 | 11/1995 |
| JP | 55-99189 | 7/1980 |
| JP | 57-118789 | 7/1982 |
| JP | 58-16685 | 1/1983 |

(Continued)

OTHER PUBLICATIONS

Hojima et al. "Cleavage of Type I Procollagen by C- and N-Proteinases is More Rapid if the Substrate is Aggregted with Dextran Sulfate or Polyethylene Glycol" Anal. Biochem. (1994) 223: 173-180.*

(Continued)

*Primary Examiner*—L. Blaine Lankford
*Assistant Examiner*—Susan Hanley
(74) *Attorney, Agent, or Firm*—Sterne, Kessler, Goldstein & Fox P.L.L.C.

(57) ABSTRACT

Methods are provided for the stabilization of proteinases by the covalent attachment of or admixture with water-soluble polymers. The resultant stabilized proteinases have increased stability under the harsh conditions used in industrial genomics, which permits their use in the extraction and isolation of nucleic acids and the identification of disease-related prion proteins at elevated temperatures in solutions containing chaotropic agents, such as sodium dodecyl sulfate, urea or guanidinium salts, conferring advantages for robotic applications.

42 Claims, 18 Drawing Sheets

FOREIGN PATENT DOCUMENTS

| | | |
|---|---|---|
| JP | 62-55079 | 3/1987 |
| WO | WO 96/11953 A1 | 4/1996 |
| WO | WO 98/35026 A1 | 8/1998 |
| WO | WO 99/00489 A1 | 1/1999 |
| WO | WO 99/48918 A1 | 9/1999 |
| WO | WO 00/04138 A1 | 1/2000 |
| WO | WO 00/07629 A3 | 2/2000 |
| WO | WO 01/59078 A2 | 8/2001 |

OTHER PUBLICATIONS

Stauffer et al. "Inactivation of substilisin Carlsberg in surfactant and salt solutions" Biochim. Biophys. Acta, Protein Structure (1973) 295(2): 457-466.*

Ebeling et al. "Proteinase K from Tritirachium album Limber" Eur. J. Biochem. (1974) 47:91-97.*

Arakawa, T., et al., "Reversibility of Acid Denaturation of Recombinant Interferon-v" *Biopolymers* 29:1065-1068, John Wiley & Sons, Inc. (1990).

Bajorath, J., et al., "Autolysis and inhibition of proteinase K, a subtilisin-related serine proteinase isolated from the fungus *Tritirachium album* Limber," *Biochim. Biohys. Acta* 954:176-182, Elsevier Science B.V. (1988).

Bhat, T.N., et al., "The PDB data uniformity project," *Nucl. Acids Res.* 29:214-218, Oxford University Press (Jan. 2001).

Blake, M.S., et al., "A Rapid, Sensitive Method for Detection of Alkaline Phosphatase-Conjugated Anti-antibody on Western Blots," *Anal. Biochem.* 136:175-179, Academic Press, Inc. (1984).

Butler, M.J., et al., "Cloning and Characterization of a Gene Encoding a Secreted Tripeptidyl Aminopeptidase from *Streptomyces lividans* 66," *Appl. Environ. Microbiol.* 61:3145-3150, American Society for Microbiology (1995).

Caetano-Anollés, G., et al., "DNA Amplification Fingerprinting Using Very Short Abitrary Oligonucleotide Primers," *Bio/Technology* 9:553-557, Nature Publishing Co. (1991).

Caughey, B., et al., "Scrapie Infectivity Correlates with Converting Activity, Protease Resistance, and Aggregation of Scrapie-Associated Prion Protein in Guanidine Denaturation Studies," *J. Virol.* 71:4107-4110, American Society for Microbiology (1997).

Cheng, T.-L., et al., "Accelerated Clearance of Polyethylene Glycol-Modified Proteins by Anti-Polyethylene Glycol IgM," *Bioconjugate Chem.* 10:520-528, American Chemical Society (1999).

Davis, S., et al., "Alteration of the circulating life and antigenic properties of bovine adenosine deaminase in mice by attachment of polyethylene glycol," *Clin. Exp. Immunol.* 46:649-652, Blackwell Scientific Publications (1981).

Flambard, B., and Juillard, V., "The Autoproteolysis of *Lactococcus lactis* Lactocepin III Affects Its Specificity towards β-Casein," *Appl. Environ. Microbiol.* 66:5134-5140, American Society for Microbiology (Dec. 2000).

Fuke, I., et al., "Synthesis of poly (ethylene glycol) derivatives with different branchings and their use for protein modification," *J. Control. Release* 30:27-34, Elsevier Science B.V. (1994).

Goldenberger, D., et al., "A Simple 'Universal' DNA Extraction Procedure Using SDS and Proteinase K is Compatible with Direct PCR Amplification," *PCR Methods Appl.* 4:368-370, Cold Spring Harbor Laboratory Press (1995).

Gunkel, F.A., and Gassen, H. G., "Proteinase K from *Tritirachium album Limber*," *Eur. J. Biochem.* 179:185-194, Blackwell Science Ltd. (1989).

He, Z., et al., "Kinetic study of thermal inactivation for native and methoxypolyethylene glycol modified trypsin," *Process Biochem.* 35:1235-1240, Elsevier Science Ltd. (Jul. 2000).

Heath, D.D., et al., "PCR primed with VNTR core sequences yields species specific patterns and hypervariable probes," *Nucl. Acids Res.* 21:5783-5785, Oxford University Press (1993).

Hershfield, M.S., et al., "Treatment of Adenosine Deaminase Deficiency with Polyethylene Gycol-Modified Adenosine Deaminase," *New Engl. J. Med.* 316:589-596, Massachusetts Medical Society (1987).

Hilz, H., et al., "Stimulation of Proteinase K Action by Denaturing Agents: Application to the Isolation of Nucleic Acids and the Degradation of 'Masked' Proteins," *Eur. J. Biochem.* 56:103-108, Blackwell Science Ltd. (1975).

Hilz, H., and Fanick, W., "Divergent Denaturation of Proteases by Urea and Dodecylsulfate in the Absence of Substrate," *Hoppe-Seyler's Z. Physiol. Chem.* 359:1447-1450, Walter de Gruyter & Co. (1978).

Hossain, A.M., et al., "Modified guanidinium thiocyanate method for human sperm DNA isolation," *Mol. Hum. Reprod.* 3:953-956, Oxford University Press (1997).

Iakunitskaia, L.M., et al., "Preparation of Subtilisin BPN' and Dextrane Conjugates," *Prikl. Biokhim. Mikrobiol.* 16:232-237, Nauka (1980).

Kelly, S.J., et al., "Diabetes Insipidus in Uricase-Deficient Mice: A Model for Evaluating Therapy with Poly(Ethylene Glycol)-Modified Uricase," *J. Am. Soc. Nephrol.* 12:1001-1009, American Society of Nephrology (May 2001).

Lamango, N.S., et al., "The endopeptidase activity and the activation by C1 of angiotensin-converting enzyme is evolutionarily conserved: purification and properties of an angiotensin-converting enzyme from the housefly, *Musca domestica,*" *Biochem. J.* 314:639-646, Portland Press (1996).

Lin, J.-J., et al., "A PCR-based DNA fingerprinting technique: AFLP for molecular typing of bacteria," *Nucl. Acids Res.* 24:3649-3650, Oxford University Press (1996).

McKinley, M.P., et al., "A Protease-Resistant Protein Is a Structural Component of the Scrapie Prion," *Cell* 35:57-62, Massachusetts Institute of Technology (1983).

Merrill, E.W., "Poly(ethylene oxide) star molecules: Synthesis, characterization, and applications in medicine and biology," *J. Biomater. Sci. Polymer Edn.* 5:1-11, VSP (1993).

Mintz, G.R., "An Irreversible Serine Protease Inhibitor," *BioPharm* 6:34-37, Aster Pub. (1993).

Müller, A., et al., "Crystal Structure of Calcium-free Proteinase K at 1.5-Å Resolution," *J. Biol. Chem.* 269:23108-23111, The American Society for Biochemistry and Molecular Biology, Inc. (1994).

Narhi, L.O., et al., "Stoichiometric Complexation of Streptomyces Subtilisin Inhibitor and Subtilisin," *J. Protein Chem.* 10:385-389, Plenum Publishing Corporation (1991).

Oesch, B., et al., "Properties of the Scrapie Prion Protein: Quantitative Analysis of Protease Resistance," *Biochem.* 33:5926-5931, American Chemical Society (1994).

Pähler, A., et al., "Three-dimensional structure of fungal proteinase K reveals similarity to bacterial subtilisin," *EMBO J.* 3:1311-1314, IRL Press Ltd. (1984).

Porteous, L.A., et al., "An Effective Method to Extract DNA from Environmental Samples for Polymerase Chain Reaction Amplification and DNA Fingerprint Analysis," *Curr. Microbiol.* 29:301-307, Springer-Verlag (1994).

Rocca, M., et al., "Pathophysiological and histomorphological evaluation of polyacryloylmorpholine vs polyethylene glycol modified superoxide disutase in a rat model of ischaemia/reperfusion injury," *Int. J. Artif. Organs* 19:730-734, Wichtig Editore (1996).

Sakane, T., and Pardridge, W.M., "Carboxyl-directed Pegylation of Brain-derived Neurotrophic Factor Markedly Reduces Systemic Clearance with Minimal Loss of Biologic Activity," *Pharm. Res.* 14:1085-1091, Plenum Publishing Corporation (1997).

Samal, B.B., et al., "Isolation and thermal stability studies of two novel serine proteinases from the fungus *Tritirachium album* Limber," *Enzyme Microb. Technol.* 13:66-70, IPC Science and Technology Press (1991).

Sayle, R.A., and Milner-White, E.J., "RASMOL: biomolecular graphics for all," *Trends Biochm. Sci.* 20:374-376, International Union of Biochemistry and Molecular Biology (1995).

Scott, M.R., et al., "Compelling transgenetic evidence for transmission of bovine spongiform encephalopathy prions to humans," *Proc. Natl. Acad. Sci. USA* 96:15137-15142, National Academy of Sciences (1999).

Sherman, M.R., et al., "Conjugation of High-Molecular Weight Poly(ethylene glycol) to Cytokines: Granulocyte-Macrophage Colony-Stimulating Factors as Model Substrates," in *Poly(ethylene*

*glycol). Chemistry and Biological Applications*, Harris, J.M., and Zalipsky, S., Eds., American Chemical Society, Washington, DC, pp. 155-169 (1997).

Siezen, R.J., et al., "Homology modelling and protein engineering strategy of subtilases, the family of subtilisin-like serine proteinases," *Protein Eng. 4*:719-737, Oxford University Press (1991).

Strauss, W.M., "Preparation of Genomic DNA from Mammalian Tissue," in *Current Protocols in Molecular Biology*, vol. 2, Ausubel, F.M., et al., Eds., John Wiley & Sons, Inc., New York, NY, pp. 2.2.1-2.2.3 and A.4.20 (1998).

Trowbridge, P.W., and Frisque, R.J., "Identification of three new JC virus proteins generated by alternative splicing of the early viral mRNA," *J. Neurvirol. 1*:195-206, Stockton Press (1995).

Tsai, N., et al., "Sensitive Measurement of Polyethylene Glycol-Modified Proteins," *BioTechniques 30*:396-400 and 402, Eaton Publishing Co. (Feb. 2001).

Tsang, V.C.W., et al., "Calibration of Prestained Protein Molecular Weight Standards for Use in the 'Western' or Enzyme-Linked Immunoelectrotransfer Blot Techniques," *Anal. Biochem. 143*:304-307, Academic Press, Inc. (1984).

von Specht, B.-U., et al., "Polyvinylpyrrolidone as a Soluble Carrier of Proteins," *Hoppe-Seyler's Z. Physiol. Chem. 354*:1659-1660, Walter de Gruyter & Co. (1973).

Vos, P., et al., "AFLP: a new technique for DNA fingerprinting," *Nucl. Acids Res. 23*:4407-4414, Oxford University Press (1995).

Wells, J.A., and Estell, D.A., "Subtilisin—an enzyme designed to be engineered," *Trends Biochem. Sci. 13*:291-297, Elsevier Publications Cambridge (1988).

Welsh, J., and McClelland, M., "Fingerprinting genomes using PCR with arbitrary primers," *Nucl. Acids Res. 18*:7213-7218, Oxford University Press (1990).

Wilchek, M., et al., "Affinity Chromatography," *Meth. Enzymol. 104*:3-55, Academic Press, Inc. (1984).

Williams, J.G.K., et al., "DNA polymorphism amplified by arbitrary primers are useful as genetic makers," *Nucl. Acids Res. 18*:6531-6535, Oxford University Press (1990).

Wolf, W.M., et al., "Inhibition of Proteinase K by Methoxysuccinyl-Ala-Ala-Pro-Ala-chloromethyl Ketone. An X-Ray Study at 2.2-Å Resolution," *J. Biol. Chem. 266*:17695-17699, The American Society for Biochemistry and Molecular Biology, Inc. (1991).

Unverified English language abstract for Japanese Patent Publication No. 55-99189, Document AL1, Japan Patent Office (1980).

Dialog File 351, Accession No. 7106349, Derwent WPI Unverified English language abstract for Japanese Patent Publication No. 62-55079, Document AM1, Derwent Information Ltd. (1987).

Inada, Y. et al., "Biomedical and biotechnological applications of PEG- and PM-modified proteins," *Trends Biotechnol.* 13:86-90 (1995).

Kodera, Y. et al., "Stabilization of L-asparaginase modified with comb-shaped poly (ethylene glycol) derivatives, in vivo and in vitro," *Bioconj. Chem.* 5:283-286 (1994).

Yang, Z. et al., "Polyethylene glycol-induced stabilization of subtilisin," *Enzyme Microb. Technol.* 18:82-89 (1996).

Supplementary European Search Report for European Patent Appl. No. 02744682.2, issued Oct. 25, 2004.

Ohta, M., et al., "A Dextran-Protease Conjugate for Cosmetic Use," *Cosmetics & Toiletries Magazine 111*:79-88 (Jun. 1996).

Unverified English language abstract for Japanese Patent Publication No. 57-118789, Document AP3, Dialog File 351 (Derwent WPI), Acc. No. 3525335 (accessed Aug. 15, 2003).

Unverified English language abstract for Japanese Patent Publication No. 58-16685, Document AL4, Dialog File 351 (Derwent WPI), Acc. No. 3652752 (accessed Aug. 15, 2003).

Unverified English language abstract for Japanese Patent Publication No. 62-55079, Document AM1, Japan Patent Office (1998).

Unverified partial English language translation for Japanese Patent Publication Nos. 55-99189 and 62-55079, Document Nos. AL1 and AM1, Nobuo Ogawa, Ph.D. (1997).

\* cited by examiner

Ala 1

| Table 1 |||||
|---|---|---|---|---|
| Summary of Initial Half Lives ( $T_{1/2}$ ) of Activities of Proteinase K and 5-kDa PEG Conjugates |||||
| Preincubation at 52°C without Denaturant |||||
| Sample | Mean PEG Strands * Coupled per Proteinase K | $T_{1/2}$ (minutes) | $T_{1/2}$, Fold Increase ||
| Purified Proteinase K | 0 | 16 | 1 ||
| PK + 18 mM NPC-PEG | 1.6 | 627 | 39 ||
| PK + 36 mM NPC-PEG | 3.6 | 1,222 | 76 ||
| PK + 20 mM PEG-Aldehyde, Peak Fraction | 4.6 | 1,061 | 66 ||
| PK + 30 mM PEG-Aldehyde, Peak Fraction | 6.3 | 1,407 | 88 ||
| Preincubation at 52°C with 0.5% SDS |||||
| Sample | Mean PEG Strands Coupled per Proteinase K | $T_{1/2}$ (minutes) | $T_{1/2}$, Fold Increase ||
| Purified Proteinase K | 0 | 7 | 1 ||
| PK + 18 mM NPC-PEG | 1.6 | 76 | 11 ||
| PK + 36 mM NPC-PEG | 3.6 | 180 | 25 ||
| PK + 20 mM PEG-Aldehyde, Peak Fraction | 4.6 | 191 | 27 ||
| PK + 30 mM PEG-Aldehyde, Peak Fraction | 6.3 | 194 | 27 ||
| Preincubation at 52°C with 2 M Urea |||||
| Sample | Mean PEG Strands Coupled per Proteinase K | $T_{1/2}$ (minutes) | $T_{1/2}$, Fold Increase ||
| Purified Proteinase K | 0 | 17 | 1 ||
| PK + 18 mM NPC-PEG | 1.6 | 192 | 11 ||
| PK + 36 mM NPC-PEG | 3.6 | 246 | 15 ||
| PK + 20 mM PEG-Aldehyde, Peak Fraction | 4.6 | 220 | 13 ||
| PK + 30 mM PEG-Aldehyde, Peak Fraction | 6.3 | 239 | 14 ||
| Preincubation at 52°C with 0.1 M GdnSCN |||||
| Sample | Mean PEG Strands Coupled per Proteinase K | $T_{1/2}$ (minutes) | $T_{1/2}$, Fold Increase ||
| Purified Proteinase K | 0 | 41 | 1 ||
| PK + 18 mM NPC-PEG | 1.6 | 451 | 11 ||
| PK + 36 mM NPC-PEG | 3.6 | 952 | 23 ||
| PK + 20 mM PEG-Aldehyde, Peak Fraction | 4.6 | 993 | 24 ||
| PK + 30 mM PEG-Aldehyde, Peak Fraction | 6.3 | 1,082 | 26 ||

* The mean number of PEG strands was determined by quantitation of SDS-PAGE analyses.

FIGURE 12

POLYMER CONJUGATES OF PROTEINASES

CROSS REFERENCE TO RELATED APPLICATIONS

The present application is a continuation-in-part of, and claims priority under 35 U.S.C. §120 to, commonly owned U.S. application Ser. No. 10/103,128 filed Mar. 22, 2002, now abandoned, which is a continuation-in-part of, and claims priority under 35 U.S.C. §120 to, commonly owned U.S. application Ser. No. 09/894,071, filed Jun. 28, 2001, now abandoned, the contents of each of which are entirely incorporated herein by reference.

BACKGROUND OF THE INVENTION

1. Field of the Invention

This invention relates to stabilized proteinases and methods for their manufacture and use. Specifically, this invention relates to proteinases that have been stabilized by admixture with water-soluble polymers or by conjugation of one or more strands of water-soluble polymer to sites on the proteinase.

2. Related Art

Proteinases are enzymes that are widely used in industrial genomics during the extraction and purification of DNA and RNA from cells and viruses. As used herein, "industrial genomics" refers to the commercial applications of DNA sequencing, fragment analysis and linear gene mapping. Examples of industrial genomics include the sequencing or diagnostic fragmentation of a portion of the DNA from human or animal cells for forensic purposes or to detect the presence of a gene associated with a malignancy or other disease. When nucleic acids are extracted from cells or tissues, the crude preparations include enzymes called nucleases that can catalyze the degradation of nucleic acids and thereby destroy the information encoded in their sequences. Classical methods for removing proteins, including nucleases, from preparations of nucleic acids include the precipitation of proteins by phenol, followed by precipitation of the nucleic acids by alcohol. Such methods do not adequately protect the nucleic acids from degradation.

More recent strategies for the purification of nucleic acids can involve the addition of proteinases to inactivate the nucleases and thereby protect the integrity of the nucleic acids (Strauss, W. M. (1998) in Ausubel, F. M., et al., (eds.) *Current Protocols in Molecular Biology*, Vol. 2, Unit 2.2, New York: John Wiley & Sons). The dissociation of tissues and the extraction of intact nucleic acids would be facilitated by the addition of chaotropic agents as well as proteinases, but the available proteinases are rapidly inactivated by the chaotropic agents. Proteinases (also referred to as proteases) catalyze the breakdown of proteins into fragments that include polypeptides, oligopeptides and amino acids. Certain proteinases (termed "endoproteinases") cleave peptide bonds in the interior of the polypeptide chain, producing shorter peptide chains. Other proteinases (termed "exoproteinases") cleave only one or a few residues at the amino or carboxyl terminal, thereby reducing the length of the protein or peptide substrate by one or a few residues in each cleavage cycle (Butler, M. J., et al., (1995) App Environ Microbiol 61:3145–3150; Lamango, N. S., et al., (1996) Biochem J 314:639–646).

In addition to their use in industrial genomics, proteinases can be used in the identification of pathology-related prions in the molecular diagnosis of transmissible spongiform encephalopathies such as scrapie, mad-cow disease and new variant Creutzfeldt Jakob Disease (McKinley, M. P., et al., (1983) Cell 35:57–62; Oesch, B., et al., (1994) Biochemistry 33:5926–5931; Caughey, B., et al., (1997) J Virol 71:4107–4110; Scott, M. R., et al., (1999) Proc Natl Acad Sci U S A 96:15137–15142).

The first step in the action of a proteinase involves the binding of its substrate to a specific domain of the enzyme. During or following such binding, a portion of the proteinase, herein termed the "active site" or "catalytic site," interacts with the substrate to accelerate its cleavage. Proteinases with narrow specificities bind to and accelerate the digestion of a limited range of protein substrates. Other proteinases digest a wider variety of protein substrates. Insights into the binding of substrates and the catalytic properties of proteinases and other enzymes can be provided by analyses of the three-dimensional structures of their active conformations (Pähler, A., et al., (1984) EMBO J 3:1311–1314).

Since many applications of proteinases involve the cleavage of protein substrates in their interior, endoproteinases have wide utility in industry. Examples of endoproteinases include Pronase, an enzyme from *Streptomyces griseus* (EC 3.4.24.31), members of the family of bacterial subtilisin-like serine proteases ("subtilases"), such as subtilisin Carlsberg (EC 3.4.21.62), and three fungal enzymes (all from *Tritirachium album*): Proteinase K (EC 3.4.21.64), ProteinaseR and ProteinaseT (Samal, B. B., et al., (1991) Enzyme Microb Technol 13:66–70). The broad specificities of these enzymes, particularly the subtilases, make them valuable reagents in industrial genomics. The disadvantages of using these enzymes, however, include their vulnerability to self-digestion during storage and use, particularly at elevated temperatures (Bajorath, J., et al., (1988) Biochim Biophys Acta 954:176–182). Consequently, efforts have been made to increase their stability. U.S. Pat. No. 5,246,849 (Bryan, P. N., et al.); U.S. Pat. No. 5,278,062 (Samal, B. B., et al.); U.S. Pat. No. 5,837,517 (Sierkstra, L. N., et al.); U.S. Pat. No. 6,190,900 (Sierkstra, L. N., et al.); and U.S. Pat. No. 6,300,116 (Von der Osten, C. et al.) describe examples of proteinases the stability of which was improved by molecular and genetic techniques. Examples of chemically-derivatized proteases with enhanced performance for cleaning surfaces and fabrics are described by Olsen, A. A., et al., in U.S. Pat. Nos. 5,856,451; 5,981,718; 6,114,509 and 6,201,110 and by Bauditz, P., et al., in PCT publication WO 00/04138 A1 (pending as EP 1 098 964), each of which is incorporated herein fully by reference.

Unfortunately, most proteinases, including ProteinaseK and other subtilases, are susceptible to inactivation under conditions that are desirable for nucleic acid extraction for industrial applications, particularly as adapted to high throughput robotic instruments. Inactivation of proteinases is accelerated by exposure to heat and/or certain alterations in their ionic environment and by the presence of chaotropic agents, exemplified by guanidinium thiocyanate ("GdnSCN"), guanidinium hydrochloride, urea and anionic detergents such as lithium dodecyl sulfate or sodium dodecyl sulfate ("SDS"). Thus, there is a compelling need for proteinases that retain their activity under harsh conditions, such as the elevated temperatures and the presence of the denaturants that can be advantageously used in molecular diagnostics and industrial genomics.

Since the 1970s, attempts have been made to use the covalent attachment of polymers to improve the safety and efficacy of various enzymes for pharmaceutical use (Davis, F. F., et al., U.S. Pat. No. 4,179,337). Some examples include the coupling of poly(ethylene oxide) ("PEO") or poly(ethylene glycol) ("PEG") to adenosine deaminase (EC 3.5.4.4) for use in the treatment of severe combined immunodeficiency disease (Davis, S., et al., (1981) Clin Exp Immunol 46:649–652; Hershfield, M. S., et al, (1987) N Engl J Med 316:589–596). Other examples include the coupling of PEG to superoxide dismutase (EC 1.15.1.1) for the treatment of inflammatory conditions (Saifer, M., et al., U.S. Pat. Nos. 5,080,891 and 5,468,478) and to urate oxidase (EC 1.7.3.3) for the elimination of excess uric acid from the blood and urine (Inada, Y., Japanese Patent Application No. 55-099189; Williams, L. D., et al., PCT publication WO 00/07629 A3; Kelly, S. J., et al., (2001) J Am Soc Nephrol 12:1001–1009; Sherman, M. R., et al., (2001) PCT publication WO 01/59078 A2). Such polymer-conjugated enzymes, which were designed for therapeutic use, do not need to retain their activities under the harsh conditions used in industrial applications.

Poly(ethylene oxide) and poly(ethylene glycol) are polymers composed of covalently linked ethylene oxide units. These polymers have the general structure

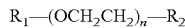

$R_1$—$(OCH_2CH_2)_n$—$R_2$ where $R_2$ may be a hydroxyl group (or a reactive derivative thereof) and $R_1$ may be hydrogen (as in PEG diol), a methyl group (as in monomethoxy PEG) or another lower alkyl group (e.g., as in iso-propoxy PEG or t-butoxy PEG). The parameter n in the general structure of PEG indicates the number of ethylene oxide units in the polymer and is referred to herein as the "degree of polymerization." PEGs and PEOs can be linear, branched (Fuke, I., et al., (1994) J Control Release 30:27–34) or star-shaped (Merrill, E. W., (1993) J Biomater Sci Polym Ed 5:1–11). PEGs and PEOs are amphipathic, i.e. they are soluble in water and in certain organic solvents and they can adhere to lipid-containing materials, including enveloped viruses and the membranes of animal and bacterial cells. The covalent attachment of PEG to a protein or other substrate is referred to herein as "PEGylation." Certain random or block or alternating copolymers of ethylene oxide ($OCH_2CH_2$) and propylene oxide (shown below)

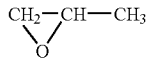

have properties that are sufficiently similar to those of PEG that these copolymers can be substituted for PEG in many applications (Hiratani, H., U.S. Pat. No. 4,609,546; Saifer, M., et al., U.S. Pat. No. 5,283,317). The term "poly(alkylene oxides)" and the abbreviation "PAOs" are used herein to refer to such copolymers, as well as to poly(ethylene glycol) or poly(ethylene oxide) and poly(oxyethylene-oxymethylene) copolymers (Pitt, C. G., et al., U.S. Pat. No. 5,476,653).

Certain polymer-modified proteinases in the prior art are claimed to have improved properties for use in laundry detergents and other washing applications (Bauditz, P., et al. and Olsen, A. A., et al., supra). However, many preparations of proteinases that are currently available contain significant quantities of impurities, including fragments of the proteinase itself, as well as unrelated contaminating proteins. Moreover, the polymer-conjugated proteinases of the prior art may contain variable amounts of both free and attached polymer, which amounts may be unknown to or inadequately described by their producers. As a result, the properties of the available polymer-coupled proteinases are variable and unpredictable, making them unsuitable for use in quantitative industrial applications. Certain polymer-conjugated proteinases of the prior art contain an unstable linkage between the polymer and the enzyme (e.g., those described in Harris, J. M., U.S. Pat. No. 6,214,966). Such conjugates can deteriorate during storage, even at 0–8° C., and are especially labile under the conditions used in industrial applications. Thus, there is a need for proteinases that have longer storage lives and greater stability during use than those that are currently available.

BRIEF SUMMARY OF THE INVENTION

The present invention provides improved proteinases and proteinase compositions that are resistant to the loss of catalytic function during storage and under harsh conditions of use.

The present invention also provides methods for improving proteinases to increase their stability and resistance to loss of catalytic activity at elevated temperatures and in solutions of chaotropic agents.

The present invention also provides proteinases having improved stability, while conserving the substrate specificity and a substantial fraction of the catalytic activity of the enzyme used as the starting material for polymer coupling (the "initial enzyme").

In certain embodiments, the invention provides chemical derivatives of proteinases, including Proteinase K and other subtilases, in which one or more strands of one or more polymers, such as poly(alkylene oxides), are covalently attached to the enzymes under rationally selected conditions. Certain reactive derivatives ("activated" forms) of these polymers can interact preferentially with amino groups, such as the alpha amino group of the amino-terminal amino acid residue or the epsilon amino groups of the lysine residues of a proteinase. Among the potential sites of attachment, such activated polymers tend to react preferentially with amino groups that are exposed on the solvent-accessible surface of the target protein, where the attachment of the polymer is least likely to be hindered sterically.

In certain additional embodiments of this invention, the amount of polymer that is attached is controlled to optimize both the stability and the catalytic activity of Proteinase K. Preferential coupling of polymers to the amino-terminal residue and/or lysine residues that are remote from the catalytic site can permit the retention of a substantial fraction of the catalytic activity of the unmodified enzyme. Such coupling can confer unexpected stability at elevated temperatures in the absence or presence of chaotropic agents such as urea, guanidinium salts or detergents. In certain additional embodiments of this invention, an optimized concentration of polymer is contacted with a proteinase solution to confer unexpected stability upon the proteinase, without covalent coupling of the polymer to the proteinase.

In certain additional embodiments, the invention provides methods of isolating nucleic acid molecules from a variety of sources, including cells, tissues, organs and organisms. Methods according to this aspect of the invention may comprise one or more steps, such as: (a) obtaining a source of nucleic acid molecules (such as a virus, cell, tissue, organ or organism); (b) placing the nucleic acid source into a solution comprising one or more of the polymer-proteinase conjugates or compositions of the invention, under conditions favoring the release of the nucleic acid molecules from the source into the solution; and (c) isolating the nucleic acid molecules. Such methods of the invention may comprise one or more additional steps, such as inserting the isolated nucleic acid molecule into a host cell or into a vector (which may be an expression vector, and which subsequently may be inserted into a host cell). In certain such methods, the isolated nucleic acid molecule may be amplified prior to insertion into the vector or host cell. The invention also provides vectors and host cells produced by such methods.

In additional embodiments, the invention provides methods of synthesizing or amplifying nucleic acid molecules. Methods according to this aspect of the invention may comprise one or more steps, such as: (a) obtaining a source of nucleic acid molecules (such as a virus, cell, tissue, organ or organism); (b) placing the nucleic acid source into a solution comprising one or more of the polymer-proteinase conjugates or compositions of the invention, under conditions favoring the release of the nucleic acid molecules from the source into the solution; (c) adding a protease inhibitor and (d) amplifying the nucleic acid molecules in the solution. In certain such aspects of the invention, the nucleic acid molecules may be isolated prior to, or in some embodiments, after, being amplified. Such methods of the invention may comprise one or more additional steps, such as inserting the synthesized (i.e., amplified) nucleic acid molecule into a host cell or into a vector (which may be an expression vector, and which subsequently may be inserted into a host cell). In certain such methods, the synthesized (i.e., amplified) nucleic acid molecule may be further amplified prior to insertion into the vector or host cell. The invention also provides vectors and host cells produced by such methods.

In additional embodiments, the invention provides methods of sequencing nucleic acid molecules. Methods according to this aspect of the invention may comprise one or more steps, such as: (a) obtaining a source of nucleic acid molecules (such as a virus, cell, tissue, organ or organism); (b) placing the nucleic acid source into a solution comprising one or more of the polymer-proteinase conjugates or compositions of the invention, under conditions favoring the release of the nucleic acid molecules from the source into the solution; (c) isolating the nucleic acid molecules from the solution; and (d) determining the nucleotide sequence of the isolated nucleic acid molecules. In certain such aspects of the invention, the nucleic acid molecules may be amplified prior to being sequenced. For certain applications, such methods of the invention may comprise one or more additional steps, such as comparing the nucleotide sequence of the isolated nucleic acid molecules to the nucleotide sequence of one or more other nucleic acid molecules, to determine the similarities and/or differences between the molecules.

In additional aspects, the invention provides methods of detecting the presence of a nucleic acid molecule associated with a disease or disorder (e.g., a genetic marker of cancer or a genetic defect associated with an inherited metabolic disorder). Methods of detecting the presence of a disease-associated nucleic acid molecule in a sample according to this aspect of the invention may involve one or more steps, such as: (a) obtaining a nucleic acid source (such as a cell, tissue, organ or organism) to be analyzed for the presence of a disease-associated nucleic acid molecule; (b) placing the source into a solution comprising one or more of the polymer-proteinase conjugates or compositions of the invention, under conditions such that the nucleic acid molecules in the source are released from the source into the solution; (c) adding a protease inhibitor and (d) detecting the presence of a disease-associated nucleic acid molecule in the solution. The nucleic acid molecules obtained from the source may be isolated and/or amplified prior to being analyzed for the presence of the disease-associated nucleic acid molecule. Disease-associated nucleic acid molecules may be detected in such methods of the invention using methods known in the art, such as polymerase chain reaction ("PCR"), Southern blotting, Northern blotting, Western blotting and enzyme-linked immunosorbent assay ("ELISA"), among others.

In additional aspects, the invention provides methods of detecting the presence of a disease- or disorder-associated prion protein molecule. Such methods, according to this aspect of the invention may involve one or more steps, such as: (a) obtaining a prion protein source (such as a cell, tissue, organ or organism) to be analyzed for the presence of a disease-associated prion protein molecule; (b) placing the source into a solution comprising one or more of the polymer-proteinase conjugates or compositions of the invention, under conditions such that the normal prion protein molecules in the source are released from the source into the solution and extensively digested by the polymer-proteinase conjugate or composition; and (c) detecting the presence in the solution of a disease-associated prion protein molecule that is resistant to digestion by the polymer-proteinase conjugate or composition (Caughey, B., et al., supra). The prion protein molecules obtained from the source may be separated by electrophoresis or other separation methods that are known in the art, prior to being analyzed for the presence of the disease-associated prion protein. Alternatively, separation of prion proteins by electrophoresis or other methods known in the art can precede the selective digestion of normal prion proteins and can be followed by detection of the disease-associated prion protein molecules. Disease-associated prion protein molecules may be detected using anti-prion antiserum in such methods of the invention using art-known methods such as Western blotting and ELISA, among others.

In additional embodiments, the invention provides compositions comprising one or more of the polymer-proteinase conjugates of the invention, which may further comprise one or more additional components or reagents, such as one or more buffer salts, one or more chaotropic agents, one or more detergents, one or more proteins, one or more polymers such as PEG and the like. The invention also provides kits comprising the polymer-proteinase conjugates and/or compositions of the invention.

BRIEF DESCRIPTION OF THE DRAWINGS

This invention is described with reference to certain embodiments thereof, some of which are illustrated in the figures listed below.

FIG. 12 ("Table 1") is a table summarizing the initial half lives (T1/2) of the proteolytic activities of conjugates of Proteinase K and 5 kDa PEG under various coupling conditions.

DETAILED DESCRIPTION OF THE INVENTION

Figure 1A:
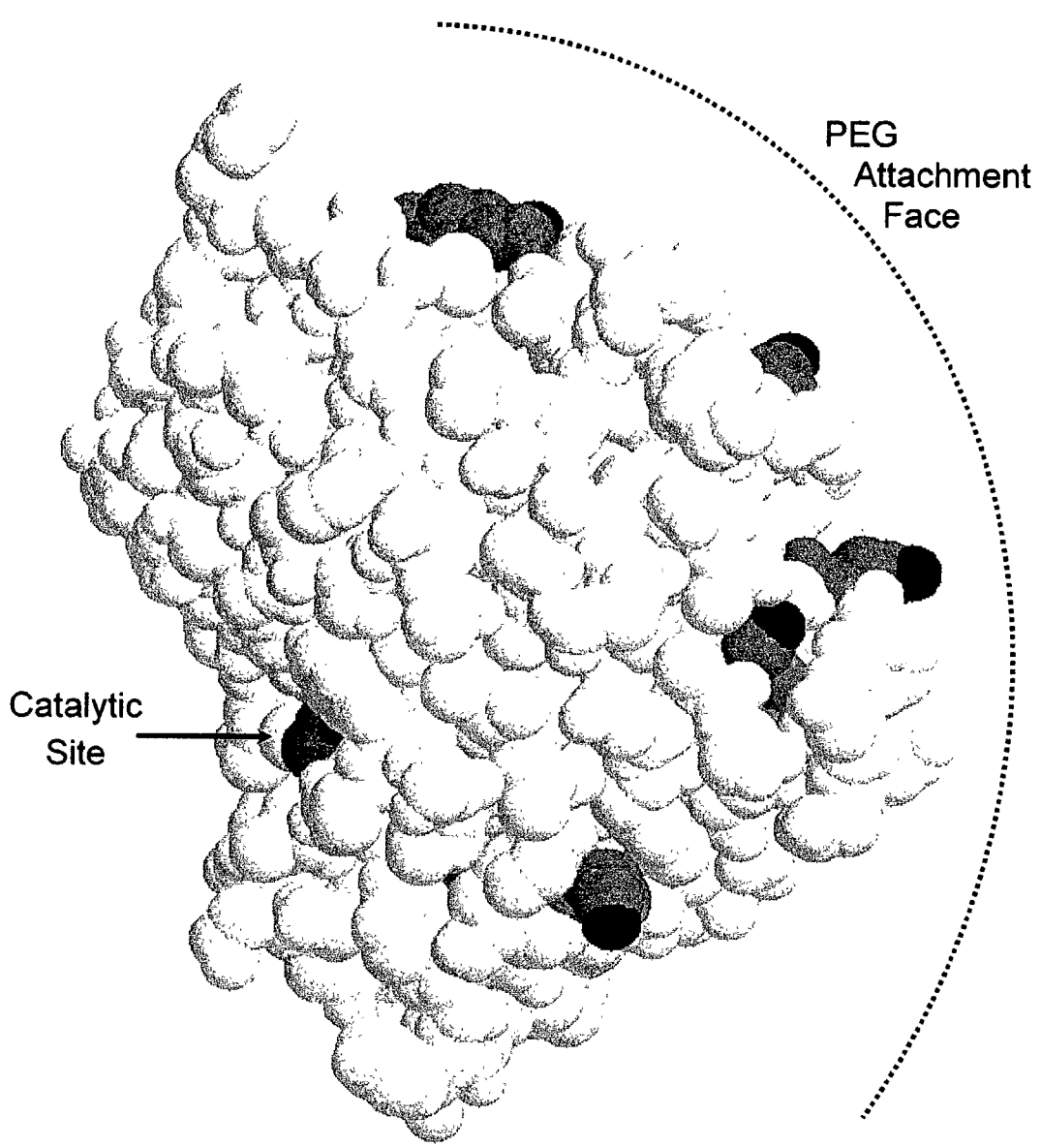
FIGS. 1a–1c depict three views of a computerized representation of the solvent-accessible surfaces of Proteinase K from *Tritirachium album*.

I. Structure and Function of Proteins, Including Proteinases

Proteins are long-chain linear polymers comprised of sequences of amino acids that are linked covalently by peptide bonds. The sequence of amino acids (referred to as the "primary structure") determines the short-range interactions that are responsible for "secondary structures," such as alpha helices and beta pleated sheets, as well as for the longer-range interactions that are responsible for the overall folding of the polypeptide chain (referred to as the "tertiary structure"). In proteins containing more than one subunit, the primary structures of the subunits ultimately determine the stability of the interactions and arrangement of the subunits in the native oligomeric or multimeric structures (referred to as the "quaternary structure"). Since detergents and agents such as urea and guanidinium salts can disrupt many features of the secondary, tertiary and quaternary structures of proteins (i.e., they induce chaos), they are referred to as "chaotropic agents." Such agents can enhance the susceptibility of the peptide bonds of a protein to hydrolytic cleavage (Hilz, H., et al., (1975) Eur J Biochem 56:103–108; Hilz, H., et al., (1978) Hoppe Seyler's Z Physiol Chem 359:1447–1450).

Proteins that accelerate the rates of chemical reactions between and among other molecules are referred to as "enzymes." Enzymes can catalyze reactions in which two or more molecules are joined together ("anabolic reactions") and/or the breakdown of molecules ("catabolic reactions"). Catabolism of proteins that involves the hydrolytic cleavage of peptide bonds is referred to as "proteolysis" and the enzymes that catalyze this process are referred to as proteinases. Proteinases are, themselves, substrates for proteolysis. Their self-digestion ("autolysis") can be promoted by exposure to elevated temperature and/or to chaotropic agents under conditions that are sufficiently harsh to disrupt their structures partially, but not sufficiently harsh to inhibit their proteolytic activity completely.

II. Stabilization of Proteinases and Other Proteins by Polymers

In one aspect, the present invention provides methods for stabilizing proteinases by the covalent attachment of polymers thereto. Such proteinases to which one or more polymers (or strands thereof) have been covalently attached are referred to herein variously and equivalently as "conjugated proteinases" or "modified proteinases." These terms are to be distinguished herein from "unconjugated proteinases," "initial proteinases" or "unmodified proteinases," by all of which is intended that the proteinases have not had one or more polymers covalently attached thereto. In another aspect, the present invention provides methods and compositions for stabilizing solutions of proteinases by the admixture of polymers thereto. It is to be understood, however, that an "unconjugated," "unmodified" or "initial" proteinase may contain other, non-polymer conjugations or modifications when compared to a wild type or native proteinase molecule, and would still be considered to be "unconjugated," "unmodified" or "initial" in accordance with the present invention, since the proteinase would be "unconjugated," "unmodified" or "initial" with respect to polymer attachment. The term "stabilizing" a proteinase (or "methods of stabilization" or "stabilized proteinase") indicates that a proteinase has been stabilized according to the methods of this invention (i.e., a proteinase to which a polymer has been covalently attached or admixed according to the methods of the invention). Such stabilized proteinases will exhibit certain altered biochemical and biophysical characteristics when compared to a proteinase that has not been stabilized (i.e., an initial proteinase to which a polymer has not been covalently attached or admixed). Included among such altered biochemical and biophysical parameters are decreased autolysis, and particularly the maintenance of the enzymatic activity of a proteinase during incubation under certain harsh environmental or experimental conditions. For example, proteinases that have been stabilized according to the methods of the present invention will advantageously display an integrated enzymatic activity at a temperature of about 50° C. or a controlled temperature in the range of about 30° C. to about 75° C. (in certain embodiments, at such a temperature over a period of time of about 1 hour to about 24 hours, about 90 minutes to about 24 hours, about 2 hours to about 18 hours, about 90 minutes to about 16 hours, about 90 minutes, or about 16 hours) that is greater than the integrated enzymatic activity of the initial proteinase. As used herein when referring to any numerical value, the term "about" means a value of ±10% of the stated value (e.g., "about 50° C." encompasses a range of temperatures from 45° C. to 55° C., inclusive; similarly, "about 100 mM" encompasses a range of concentrations from 90 mM to 110 mM). In certain such embodiments, the integrated enzymatic activity of the stabilized proteinase may be, for example, at least about 150% to at least about 300%, at least about 150% to at least about 250%, at least about 150% to at least about 200%, or at least about 150%, of the integrated enzymatic activity of the initial proteinase. Certain such methods may result in the production of stabilized proteinases that exhibit such greater integrated enzymatic activity in the presence of one or more chaotropic agents such as those described elsewhere herein.

Any proteinase can be suitably used as an initial proteinase in the present invention, including but not limited to endoproteinases such as Pronase (EC 3.4.24.31), members of the family of bacterial subtilisin-like serine proteases ("subtilases") such as subtilisin Carlsberg (EC 3.4.21.62), Proteinase K (EC 3.4.21.64), Proteinase R, Proteinase T (Samal, B. B., et al., (1991) Enzyme Microb Technol 13:66–70), and the like. As the ordinarily skilled artisan will appreciate, any proteinase known and readily available in the art is suitable for conjugation with reactive polymers, or for forming compositions with unreactive polymers, according to the present invention. In accordance with certain aspects of the invention, these initial proteinases are used to produce conjugates in which one or more polyalkylene glycols ("PAGs") (which may be alternatively and equivalently referred to herein as "polyalkylene oxides" or "PAOs") are covalently linked to the proteinase peptide molecule. The PAG polymers used in such conjugates may be linear polymers, or may be branched at one or more points along the polymer molecule. In addition, the polymers used to form the conjugates of the invention may be homopolymers, in which multiple units of a single monomer type are linked together to form the polymer, such as poly(ethylene glycol) or poly(propylene glycol), or they may be heteropolymers or copolymers (in which monomeric units of two or more structures are linked together to form the polymer, such as a poly(ethylene glycol)-poly(propylene glycol) copolymer). Polymers used in accordance with the invention may be unreactive polymers or reactive polymers. As used herein, "unreactive polymers" are those polymers that will not attach covalently to a protein, such as a protease. Examples of such "unreactive polymers" include, but are not limited to, monomethoxyPEG (mPEG), which is a linear polymer of ethylene oxide units with a hydroxyl group at one end and a methoxyl group at the other end, and by PEG diol, which is a linear polymer of ethylene oxide units with hydroxyl grups at both ends. As used herein, "reactive polymers" are those polymers that can react with solvent-accessible amino groups on a protein (such as a proteinase), including but not limited to the $\alpha$ amino group or the $\epsilon$ amino group of lysine residues. Examples of "reactive polymers" include, but are not limited to, mPEG in which the hydroxyl end group has been converted to or replaced by an electrophilic group, such as succinimidyl propionic acid (as in SPA-PEG) or a p-nitrophenylcarbonate (as in NPC-PEG), or an aldehyde as in PEG aldehyde. In addition to poly(alkylene oxides), suitable polymers may include polyvinyl alcohols, polycarboxylates, poly(vinylpyrrolidones) (von Specht, B.-U., et al., (1973) Hoppe-Seyler's Z Physiol Chem 354:1659–1660), poly D-amino acids and/or poly L-amino acids, polyacryloylmorpholine (Rocca, M., et al., (1996) Int J Artif Organs 19:730–734) and dextrans (Iakunitskaya, L. M., et al., (1980) Prikl Biokhim Mikrobiol 16:232–237). Sites on the initial proteinase molecules to which polymers advantageously may be attached include lysine residues found on the peptide molecules, which residues each have two amino groups. One of these amino groups (the alpha amino group) participates in peptide bond formation (except when the lysine is the amino-terminal residue of the protein), leaving the other amino group (the epsilon amino group) available for polymer coupling. Other sites on the proteinase peptide molecule to which polymers advantageously may be attached include, among others, the alpha amino group at the amino-terminal residue of the polypeptide; the sulfhydryl groups of cysteine residues on the proteinase peptide (Braxton, S. M., U.S. Pat. No. 5,766,897), to which polymers activated with vinyl sulfone, maleimide, iodoacetamide, bromoacetamide or orthopyridyl disulfide, among other sulfhydryl-reactive groups that are known in the art, can be coupled; the guanido groups of arginine residues on the proteinase peptide (Sano, A., et al., U.S. Pat. No. 5,093,531), to which polymers activated with phenylglyoxal can be coupled; the alpha carboxyl group of the C-terminal residue, the beta carboxyl groups of aspartate residues on the proteinase peptide and the gamma carboxyl groups of the glutamate residues on the proteinase peptide (Sakane, T., et al., (1997) Pharm Res 14:1085–1091), to which amine or hydrazide derivatives of the polymer can be coupled. Of course, other suitable sites on the proteinase peptide molecule to which one or more polyalkylene oxides advantageously may be attached will be readily apparent to one of ordinary skill in the art, particularly upon consideration of the primary and tertiary structures of the peptide.

Derivatives of PEGs, PEOs and other PAOs that react more or less selectively with various sites on the target protein are well known in the art and can be purchased from suppliers such as Fluka (Milwaukee, Wis.); NOF Corporation (Tokyo, Japan); Shearwater Corporation (Huntsville, Ala.), a subsidiary of Inhale Therapeutic Systems, Inc. (San Carlos, Calif.); Sigma Chemical Company (St. Louis, Mo.) or SunBio, Inc. (Anyang City, South Korea).

Activated forms of polymers that are suitable for use in the methods and stabilized proteinases of this invention can include any reactive forms of polymers that are known in the art. For example, PAOs of various sizes are suitable, including those with molecular weights (excluding the mass of the activating group) in the range of about 200 Daltons to about 100,000 Daltons (100 kDa). Suitable ranges of molecular weights can be about 1 kDa to about 20 kDa, about 2 kDa to about 20 kDa, about 2 kDa to about 15 kDa, about 5 kDa to about 20 kDa, about 5 kDa to about 15 kDa, about 2 kDa to about 10 kDa, about 5 kDa to about 10 kDa, or about 2 kDa to about 5 kDa. In the case of PEGs, the molecular weight range of about 2 kDa to about 5 kDa corresponds to a degree of polymerization (n) in the range of about 45 to about 114 monomeric units of ethylene oxide. It should be noted that the advantages of coupling a proteinase to polymers having this relatively low range of molecular weights (i.e., 2 kDa to 5 kDa) were not observed when assays of proteolytic activity were performed with a substrate of low molecular weight (see He, Z., et al., (2000) Proc Biochem 35:1235–1240), instead of a protein substrate as disclosed herein. Other forms of polymers that are suitable for use in this invention include dextrans, poly(vinylpyrrolidone), polyacryloyl-morpholine, poly(oxyethylene-oxymethylene) copolymers and other polymers known in the art.

Before coupling a polymer to Proteinase K or another proteinase, it can be advantageous to purify the enzyme to remove the products of autolysis and other contaminants. Otherwise, the analysis of the extent of modification of the intact enzyme can be complicated by the formation of polymer conjugates of the fragments of the proteinase and other contaminants. The crude or purified enzyme can be incubated with activated polymer in a buffer having a pH in the range of about 8.5 down to the lowest pH at which any inactivation of the enzyme caused by acid can be reversed (see Arakawa, T., et al., (1990) Biopolymers 29:1065–1068). The use of a low pH for polymer coupling to proteinases can be desirable in order to suppress autolysis during derivatization, since the activities of certain proteinases have pH optima in the range of about 7.5 to 12 (Samal, B. B., et al., U.S. Pat. No. 5,278,062). However, the use of a higher pH can be advantageous for certain other proteinases and certain coupling chemistries, depending on the relative effects of pH on the rate of hydrolysis of the activated polymer (whether spontaneous or catalyzed by the proteinase) and the rate of attachment of the polymer to the target protein.

A linear polymer can optionally have a reactive group at one end or both ends, thereby creating a "reactive polymer." In certain embodiments of this invention, it can be desirable to use the succinimidyl propionic acid derivative of monomethoxy PEG ("SPA-PEG"), as described in Harris, J. M., et al., U.S. Pat. No. 5,672,662, which is incorporated herein fully by reference. In certain other embodiments, it can be desirable to use either the succinimidyl carbonate derivatives of monomethoxy PEG ("SC-PEG"), as described in Saifer, M., et al., U.S. Pat. Nos. 5,006,333; 5,080,891; 5,283,317 and 5,468,478, or the p-nitrophenyl carbonate derivative of monomethoxy PEG ("NPC-PEG"), as described in PCT publication WO 01/59078 A2, supra, Kelly, S. J., et al., supra, and in Sherman, M. R., et al. (1997) in Harris, J. M., et al., (eds.) Poly(ethylene glycol) Chemistry and Biological Applications, ACS Symposium Series Vol. 680, Washington, D.C.: American Chemical Society, pp. 155–169. Moreover, other types of reactive groups can be used to synthesize polymer conjugates of proteinases. These derivatives include aldehyde derivatives of monomethoxy PEG (Royer, G. P., U.S. Pat. No. 4,002,531; Harris, J. M., et al., U.S. Pat. No. 5,252,714), fluorophenyl carbonates, bromophenyl carbonates, chlorophenyl carbonates, thiazolidine-2-thione, triazine and carbonyldiimidazole derivatives.

It may be desirable to minimize the formation of intramolecular and intermolecular cross-links by polymers such as PEG. This can be accomplished by using polymers that are activated at only one end (referred to herein as "monofunctional PEGs") or polymer preparations in which the percentage of bifunctionally activated polymers (referred to in the case of PEGs as "bis-activate PEG diols") is less than 30%, or more preferably less than 10% or most preferably less than 2% (w/w). The use of activated polymers that are predominantly monofunctional can minimize the formation of all of the following: intramolecular cross links within an individual enzyme molecule, "dumbbell" structures, in which one strand of polymer connects two enzyme molecules, and larger aggregates or gels. When activated polymers that react with amino groups are used, the maximum theoretical number of strands of polymer that can be attached to one molecule of proteinase corresponds to the total number of amino groups. The actual number of amino groups that are accessible on the surface of a proteinase under any particular conditions of polymer coupling may be smaller than the theoretical maximum.

The use of molecular modeling can facilitate a strategy for the optimization of polymer coupling to a proteinase. X-ray crystallographic data can be used to generate computerized images of the solvent-accessible surfaces of proteins (Sayle, R. A., et al., (1995) Trends Biochem Sci 20:374–376). Structural analyses that are based on nuclear magnetic resonance measurements can also be useful in this regard. The fraction of the accessible sites on the surface with which a particular activated polymer can react, and the distribution of polymer strands among the various sites, can be modulated by selecting the appropriate activating group, the molar ratio of the polymer to the enzyme and the appropriate conditions of the coupling reaction (e.g., pH, temperature, concentrations of reactants, duration of incubation). It can be advantageous to attach the polymer to residues that are sufficiently far from the active site to minimize any adverse effects on catalytic function. For example, the surface of Proteinase K contains many potential sites for the attachment of polymers that are activated with various chemistries. However, our discovery that the most solvent-accessible lysine residues of Proteinase K are located exclusively in a region of the enzyme that is relatively far from the catalytic site makes the use of amino-reactive polymers especially desirable for this enzyme (see FIG. 1a).

Based on our analyses of the three-dimensional structure of Proteinase K, the number of strands of amine-reactive polymers that can be coupled to its amino groups without causing inactivation is less than the total of nine amino groups. In various embodiments of this invention, the number of strands of polymer attached can be varied from about one and to about nine (see FIGS. 2c and 2d). A substantial fraction of the proteolytic activity can be retained when an average of up to about seven strands of PEG are attached (see FIG. 8). The resultant conjugates are relatively stable under conditions in which the unmodified enzyme is rapidly inactivated. The combined properties of stabilization during storage in aqueous solution and preservation of catalytic activity, especially during prolonged incubation at an elevated temperature and/or in the presence of anionic detergents, urea or guanidinium salts, are unexpected on the basis of the prior art.

Figure 3:
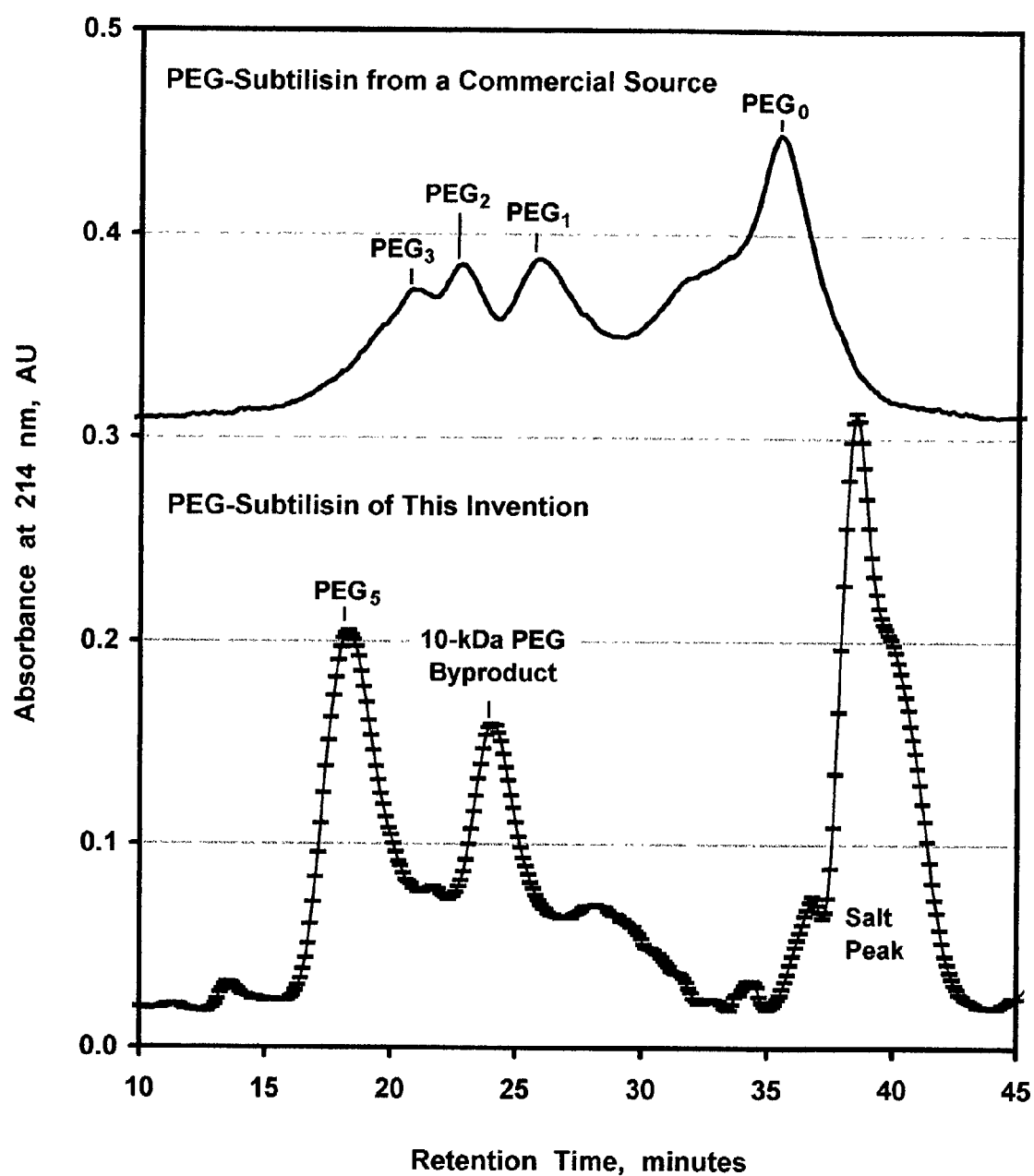
FIG. 3 displays results of size-exclusion high performance liquid chromatography ("HPLC") of PEG-subtilisin from a commercial source and of the products of reactions of subtilisin with one form of activated PEG according to this invention.

Like Proteinase K, subtilisin Carlsberg can be derivatized using the methods of this invention to yield PEG adducts that have a significantly higher extent of PEGylation than commercially available PEG-subtilisin products (see FIG. 3). The PEG-subtilisin of this invention, like the PEG-Proteinase K of this invention, would be expected to have a longer shelf life and be more stable under harsh conditions.

In certain embodiments (e.g. in the case of enzymes in which the catalytic domain contains amino acid residues (such as those described above) with which the activated polymer can react), it may be desirable to shield the active site from contact with the activated polymer. In such cases, the enzyme can be bound tightly, but reversibly, to a substrate analog or competitive inhibitor that is sufficiently large to sterically hinder the access of the activated polymer to reactive residues within or near the active site (see, e.g., Nahri, L. O., et al., (1991) J Protein Chem 10:385–389). Alternatively, such analogs or inhibitors can be bound to a solid matrix to which the proteinase can be subsequently adsorbed. While bound to the resultant "affinity matrix," the proteinase can be reacted with the activated polymer. This strategy can minimize the coupling of the reactive polymer to sites where such coupling might inhibit catalysis. The selectively modified proteinase can be released from the affinity matrix subsequently, by methods that are known to those skilled in the art (see Wilchek, M., et al., (1984) Methods Enzymol 104:3–55). The resultant conjugates can include proteinase molecules to which the polymer is preferentially attached at sites where it does not interfere with catalysis.

Following the coupling reaction, conjugates that are derivatized to various extents can be separated from each other using size-exclusion and/or ion-exchange chromatography, as described by Sherman, M. R., et al., (1997) supra. For example, chromatography on a Superdex® 75 HR 10/30 or a Superdex® 200 HR 10/30 column (Amersham Pharmacia Biotech, Piscataway, N.J.) can enable the separation of proteinase molecules that are PEGylated to different extents, as well as separating them from residual free PEG and from most byproducts of the coupling reaction (see Example 2).

III. Methods of Analysis

Other aspects of this invention relate to new methods for the analysis of polymer-modified proteinases. Accurate and reproducible determinations of the average extent of polymer modification of a proteinase and of the relative quantities of proteinase molecules that are derivatized to various extents can be obtained by individual methods or combinations of methods selected from the group including mass spectroscopy, size-exclusion chromatography, ion-exchange chromatography, capillary electrophoresis, polyacrylamide gel electrophoresis and Western blotting with antibodies to the protein and/or the polymer (Blake, M. S., et al., (1984) Anal Biochem 136:175–179; Tsang, V. C. W., et al., (1984) Anal Biochem 143:304–307; Cheng, T.-L., et al., (1999) Bioconjug Chem 10:520–528; Tsai, N., et al., (2001) BioTechniques 30:396–402).

Functional assays include the measurement of catalytic activity using polypeptide or protein substrates for proteinases, preferably under standardized conditions. As used herein, "standardized conditions" for the measurement of the activity of Proteinase K are defined as incubation for 1 hour at 52° C. of about 0.6 mcg/mL Proteinase K with 5.5 mg/mL casein (Sigma, catalog #C 7078) in 45 mM Tris-HCl buffer, pH 8. Proteinase K and the other subtilases belong to the class of enzymes known as serine proteinases, which contain a functional serine residue within the active site (Siezen R. J., et al., (1991) Protein Eng 4:719–737). Casein and hemoglobin are model substrates for such enzymes. The digestion of casein is referred to herein as "caseinolytic activity" and can be monitored spectrophotometrically or turbidimetrically, using methods known in the art (see Flambard, B., et al., (2000) Appl Environ Microbiol 66:5134–5140). Functional assays are useful for studying the effects of harsh conditions on enzymatic activity. Such conditions include exposure to elevated temperatures in the absence or presence of chaotropic agents. For example, urea, guanidinium salts and SDS are commonly used denaturing agents (Porteous, L. A., et al., (1994) Curr Microbiol 29:301–307; Goldenberger, D., et al., (1995) PCR Methods Appl 4:368–370; Hossain, A. M., et al., (1997) Mol Hum Reprod 3:953–956). Typical studies include the incubation of a sample of an unmodified or a derivatized proteinase for various periods at an elevated temperature in the presence or absence of a denaturant.

A suitable method for comparing the stability of polymer-proteinase conjugates compares the areas under the curve ("AUCs"), or the integral over a defined period of time, of graphs of residual enzymatic activity versus time of preincubation of the enzyme preparation in the absence of substrate. As a basis of comparison, the AUC obtained with a polymer-proteinase conjugate can be expressed as a ratio or percentage of the AUC for an initial, unmodified proteinase under comparable conditions. Thus, if a conjugate has an AUC that is the same as that of an unmodified proteinase, the integrated enzymatic activity (AUC) of the conjugate is 100%. As considered herein, a polymer-proteinase conjugate or composition has increased stability if the AUC of a polymer-proteinase conjugate or composition is greater than the AUC of an initial, unmodified proteinase under comparable conditions over a comparable time period. In certain embodiments, conjugates and compositions can have about one and one-half times the integrated enzymatic activity; in other embodiments, about twice the integrated enzymatic activity; in alternative embodiments, about three times the activity; and in still other embodiments, about or greater than seven times the integrated enzymatic activity of an unstabilized, unmodified proteinase (see FIG. 5). These same principles of measurement of relative enzymatic activity can be applied to solutions of proteinases with which solutions of polymer have been admixed.

IV. Compositions and Kits

In related aspects, the invention also provides stabilized proteinases produced by the methods of this invention, as well as compositions comprising such stabilized proteinases. Such compositions may optionally comprise one or more additional components, such as one or more buffer salts, one or more chaotropic agents, one or more detergents, one or more proteins (e.g., one or more enzymes), one or more polymers and the like. The compositions of this aspect of the invention may be in any form, including solid (e.g., dry powder) or solution (particularly in the form of a buffered salt solution comprising one or more of the stabilized proteinases or conjugates of the invention).

The invention also provides kits comprising the polymer-proteinase conjugates and/or compositions of the invention. Such kits typically comprise a carrier, such as a box, carton, tube or the like, having in close confinement therein one or more containers, such as vials, tubes, ampuls, bottles and the like, wherein a first container contains one or more of the polymer-proteinase conjugates and/or compositions of the present invention. The kits encompassed by this aspect of the present invention may further comprise one or more additional components (e.g., reagents and compounds) necessary for carrying out one or more particular applications of the conjugates and compositions of the present invention, such as one or more components useful for nucleic acid synthesis or amplification according to standard nucleic acid synthesis or amplification protocols (see U.S. Pat. Nos. 4,683,195 and 4,683,202, which are directed to methods of DNA amplification by PCR), one or more components useful for nucleic acid sequencing (such as media containing agarose or polyacrylamide for preparing sequencing gels, or pyrophosphatase or other components useful for detection of sequenced nucleic acids according to standard protocols for sequencing (see U.S. Pat. Nos. 4,962,020 and 5,498,523, which are directed to methods of DNA sequencing), and the like.

V. Uses

The conjugates, compositions and kits of the present invention may be used in conjunction with any application involving the use of proteinases, particularly proteinases of the subtilisin family of serine proteinases, including Proteinase K. The conjugates, compositions and kits of the present invention will find particular application in methods of manipulating nucleic acid molecules, for example in industrial genomics methods employing the extraction and/or isolation of nucleic acid molecules. Such techniques may include, for example, nucleic acid isolation, amplification, synthesis, sequencing, fragment analysis and linear gene mapping. The conjugates, compositions and kits of the present invention will find particular application in methods for detection and identification of disease-related prion protein molecules, for example in the diagnosis of transmissible and hereditary spongiform encephalopathies. Such techniques may include, for example, high throughput screening of samples of tissue from animals intended for food, samples obtained from actual or prospective blood or organ donors and samples from patients at risk.

A. Nucleic Acid Isolation

In one such application, the conjugates, compositions and kits of the invention may be used in methods for isolating nucleic acid molecules from a variety of sources. Methods according to this aspect of the invention may comprise one or more steps, for example: (a) obtaining a source of nucleic acid molecules (which may be any virus, cell, tissue, organ or organism comprising one or more nucleic acid molecules) to be isolated; (b) placing the source of nucleic acid molecules into contact, preferably in a solution, with one or more of the polymer-proteinase conjugates or compositions of the present invention, under conditions such that the nucleic acid molecules in the source are released from the source into the external milieu (e.g., into the solution); and (c) isolating the nucleic acid molecules, preferably according to standard and art-known methods of nucleic acid isolation.

Sources from which nucleic acid molecules (i.e., DNA (which may be cDNA, mDNA, genomic DNA, etc.) or RNA (including rRNA, mRNA, etc.)) may be isolated are available commercially from a number of sources, including American Type Culture Collection (ATCC; Manassas, Va.), Jackson Laboratories (Bar Harbor, Me.) and Advanced Tissue Sciences (La Jolla, Calif.), and other commercial sources that will be familiar to the ordinarily skilled artisan. Alternatively, of course, a variety of viruses, cells, tissues, organs and organisms may be obtained from natural sources or locations and used as sources of nucleic acid molecules to be isolated. Cells that may be used as starting materials may be prokaryotic (bacterial, including members of the genera *Agrobacterium, Bacillus, Bordetella, Borrelia, Chlamydia, Clostridium, Collectotrichum, Escherichia, Helicobacter, Legionella, Mycobacterium, Mycoplasma, Neisseria, Pseudomonas, Rhizobium, Salmonella, Serratia, Staphylococcus, Streptococcus, Streptomyces* and *Treponema*) or eukaryotic (including fungi or yeasts, plants, protozoans and other parasites, and animals including humans and other mammals). Any mammalian somatic cell may also be used, including blood cells (e.g. leukocytes that are accompanied by or have been separated from erythrocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other cells of the stroma (e.g., macrophages, dendritic cells and Schwann cells). Mammalian germ cells (spermatocytes and oocytes) may also be used, as may the progenitors, precursors and stem cells that give rise to the above-described somatic and germ cells. Also suitable for use as sources of nucleic acid molecules are mammalian tissues or organs such as those derived from brain, kidney, liver, pancreas, blood, bone marrow, muscle, nervous, skin, genitourinary, circulatory, lymphoid, gastrointestinal and connective tissue sources, as well as those derived from a mammalian (including human) embryo or fetus. Of course, entire organisms (prokaryotic or eukaryotic), single-celled or multi-cellular, may be used as sources of nucleic acid molecules for isolation as well. These cells, tissues, organs and organisms may be normal, or they may be pathological such as those involved in infectious diseases (caused by bacteria, fungi or yeast, viruses (including HIV) or parasites), in genetic or biochemical pathologies (e.g., cystic fibrosis, hemophilia, Alzheimer's disease, schizophrenia, muscular dystrophy or multiple sclerosis), in malignant processes, or the like.

Once the sources of nucleic acid molecules are obtained, nucleic acid molecules may be isolated therefrom by methods that are well-known in the art (see, e.g., Sambrook, J., et al., (1989) *Molecular Cloning. A Laboratory Manual,* 2nd ed., Cold Spring Harbor, N.Y.: Cold Spring Harbor Laboratory Press; Kaufman, P. B., et al., (1995) *Handbook of Molecular and Cellular Methods in Biology and Medicine,* Boca Raton, Fla.: CRC Press). Ideally, such isolation methods will rely on the use of the conjugates, compositions and kits of the invention during the extraction process, to destroy or inhibit the activity of nucleases that are released from the nucleic acid sources simultaneously with the nucleic acids themselves. In such methods, then, the conjugates or compositions of the invention will be present at working concentrations in the extraction solution that is used to release nucleic acid molecules from their sources. As used throughout the present application, "working concentration" signifies that the concentration of the conjugate or composition of the invention in the solution (e.g., the extraction solution, the amplification solution, the sequencing solution, etc.) is at or near the optimal or effective concentration necessary in that solution to destroy or inhibit the activity of nucleases by at least about 50%, at least about 60%, at least about 70%, at least about 80%, at least about 85%, at least about 90%, at least about 95% or at least about 99%, when compared to nuclease activity in extracted samples that do not contain the conjugates or compositions of the invention, nor any other proteinase. As a practical matter, the level of nuclease activity in a given sample may be readily determined by the ordinarily skilled artisan using routine methods that are well-known in the art, some of which are described elsewhere herein.

Once the nucleic acid molecules have been released or extracted from their sources using the conjugates, compositions or kits of the invention, such molecules may be isolated, if desired, by a variety of physical or biochemical means suitable for nucleic acid isolation that are well-known in the art, including gel electrophoresis, chromatography (including size-exclusion, ion-exchange, affinity and immunochromatography), density gradient centrifugation, solid phase extraction and immunoadsorption (see, e.g., Sambrook, J., et al., supra; Kaufman, P. B., et al., supra). Hence, in another aspect, the invention also provides nucleic acid molecules isolated according to these methods of the invention. Such nucleic acid molecules of the invention or those isolated according to the methods of the invention may be used in further processing, for example in methods of nucleic acid synthesis, amplification and/or sequencing as described below. Alternatively, nucleic acid molecules isolated according to this aspect of the invention may be introduced into a host cell, or into a vector (which may be an expression vector, for use in expressing a polypeptide encoded by one or more genes or open reading frames encoded by the nucleic acid molecule inserted into the vector) that may then be inserted into a host cell, to produce a host cell comprising the isolated nucleic acid molecules. Hence, in another aspect, the invention also provides vectors and host cells produced by such methods. In certain aspects of the invention, it may be advantageous to amplify the isolated nucleic acid molecules prior to their insertion into a host cell or vector, according to methods of amplification described below.

B. Nucleic Acid Synthesis or Amplification

In another application, the conjugates, compositions and kits of the invention may be used in methods for synthesis or amplification of nucleic acid molecules, particularly of nucleic acid molecules that have been isolated according to the methods of the invention described above. Methods according to this aspect of the invention may comprise one or more steps, for example: (a) obtaining a source of nucleic acid molecules (which may be any virus, cell, tissue, organ or organism comprising one or more nucleic acid molecules) to be amplified; (b) placing the source of nucleic acid molecules into contact, preferably in a solution, with one or more of the polymer-proteinase conjugates or compositions of the present invention, under conditions such that the nucleic acid molecules in the source are released from the source into the external milieu (e.g., into the solution); (c) performing one or both of the steps of (i) isolating the nucleic acid molecule, preferably as described herein and according to art-known methods of nucleic acid isolation, and/or (ii) inhibiting the proteinase activity of the polymer-proteinase conjugate or composition, preferably using one or more art-known inhibitors of proteinase activity that will be familiar to the ordinarily skilled artisan; and (d) amplifying the nucleic acid molecules, preferably according to standard and art-known methods of nucleic acid synthesis or amplification. In certain methods according to this aspect of the invention, the nucleic acid molecules may be isolated prior to and/or after being amplified. Examples of nucleic acid amplification or synthesis applications suitably using the conjugates, compositions and kits of the present invention include, but are not limited to, PCR (U.S. Pat. Nos. 4,683,195 and 4,683,202), Strand Displacement Amplification ("SDA"; U.S. Pat. No. 5,455,166; EP Application 0 684 315 A1), and Nucleic Acid Sequence-Based Amplification ("NASBA"; U.S. Pat. No. 5,409,818; EP 0 329 822 B1). Nucleic acid molecules amplified (and, if applicable, isolated) according to this aspect of the invention may be introduced into a host cell, or into a vector (which may be an expression vector, for use in expressing a polypeptide encoded by one or more genes or open reading frames encoded by the nucleic acid molecule inserted into the vector) that may then be inserted into a host cell, to produce a host cell comprising the isolated nucleic acid molecules. Hence, in another aspect, the invention also provides vectors and host cells produced by such methods.

C. Nucleic Acid Sequencing

In another aspect, the conjugates, compositions and kits of the invention may be used in methods of determining the nucleotide sequence (i.e., "sequencing") of nucleic acid molecules. For example, the conjugates, compositions and kits of the invention may be used in methods involving the sequencing or diagnostic fragmentation of a portion of the DNA from human or animal cells for forensic purposes or to detect the presence of a gene associated with a malignancy or other physical disorder or disease. Methods according to this aspect of the invention may comprise one or more steps, for example: (a) obtaining a source of nucleic acid molecules (which may be any virus, cell, tissue, organ or organism comprising one or more nucleic acid molecules) to be sequenced; (b) placing the source of nucleic acid molecules into contact, preferably in solution, with one or more of the polymer-proteinase conjugates or compositions of the present invention, under conditions such that the nucleic acid molecules in the source are released from the source into the external milieu (e.g., into the solution); and (c) sequencing the nucleic acid molecules, preferably according to standard and art-known methods of nucleic acid sequencing. In certain methods according to this aspect of the invention, the nucleic acid molecules may be amplified and/or isolated prior to being sequenced. Suitable methods for determining the nucleic acid sequence of nucleic acid molecules are well-known in the art and will be familiar to one of ordinary skill. Examples of such nucleic acid sequencing techniques that may suitably employ the present conjugates, compositions and kits include, but are not limited to, dideoxy sequencing methods such as those disclosed in U.S. Pat. Nos. 4,962,020 and 5,498,523, as well as more complex PCR-based nucleic acid fingerprinting techniques such as Random Amplified Polymorphic DNA ("RAPD") analysis (Williams, J. G. K., et al., (1990) Nucleic Acids Res 18:6531–6535), Arbitrarily Primed PCR ("AP-PCR"; Welsh, J., et al., (1990) Nucleic Acids Res 18:7213–7218), DNA Amplification Fingerprinting ("DAF"; Caetano-Anollés, G., et al., (1991) BioTechnology 9:553–557), microsatellite PCR or Directed Amplification of Minisatellite-region DNA ("DAMD"; Heath, D. D., et al., (1993) Nucleic Acids Res 21:5782–5785), and Amplification Fragment Length Polymorphism ("AFLP") analysis (EP 0 534 858 B1; Vos, P., et al., (1995) Nucleic Acids Res 23:4407–4414; Lin, J. J., et al., (1996) Nucleic Acids Res 24:3649–3650).

D. Detection of Disease-Related Nucleic Acid Molecules

In another aspect, the invention provides methods of detecting the presence of nucleic acid molecules (e.g., genes or fragments thereof, viruses, etc.) that are associated with a particular disease or physical disorder. The statement that a nucleic acid molecule is "associated with" a disease or physical disorder indicates that the presence (or absence, in certain diseases or physical disorders) of the nucleic acid molecule in a sample obtained from cells, tissues, organs or organisms is indicative of the presence of, or predisposition to, a particular disease or physical disorder. For example, the presence of certain genes or fragments thereof in animal cells and tissues, such as genes encoding carcinoembryonic antigen ("CEA"), prostate-specific antigen ("PSA"), •-feto-protein ("AFP") and certain breast cancer associated antigens (e.g., BRCA1 and BRCA2), has been associated with certain types of cancers appearing in the cells and tissues of such animals. As another example, the presence of certain proteinase-resistant prions in samples of animal brain and other tissues has been found to be associated with certain transmissible encephalopathies, such as bovine spongiform encephalopathy ("BSE," or "mad cow disease"), scrapie, progressive multifocal leukoencephalopathy ("PML"), and Creutzfeldt Jakob Disease (see McKinley, M. P., et al., supra; Oesch, B., et al., supra; Caughey, B., et al., supra; Trowbridge, P. W., et al., (1995) J Neurovirol 1: 195–206.) Hence, the presence of such nucleic acid molecules or protease resistant prions may be used as a diagnostic tool for determining the presence of or predisposition to such disorders or diseases, whether or not such nucleic acid molecules or protease-resistant prions are themselves directly involved in the etiology of such diseases or disorders.

Methods of detecting the presence of a disease-associated nucleic acid molecule in a sample according to this aspect of the invention may involve one or more steps, such as: (a) obtaining a nucleic acid source (such as those described above) to be analyzed for the presence of a disease-associated nucleic acid molecule; (b) placing the source into a solution comprising one or more of the polymer-proteinase conjugates or compositions of the invention, under conditions such that the nucleic acid molecules in the source are released from the source into the solution; and (c) detecting the presence of a disease-associated nucleic acid molecule in the solution. In certain such aspects, it will be advantageous to isolate the nucleic acid molecules from the source or the solution prior to conducting the analysis for detecting the presence of the disease-associated nucleic acid molecules in the source or solution. In other aspects, it will be advantageous to amplify the nucleic acid molecules (or, at least, any disease-associated nucleic acid molecules) obtained from the source prior to or following isolation, and/or prior to conducting the analysis for detecting the presence of the disease-associated nucleic acid molecules in the source or solution. Any suitable method of detection of a particular nucleic acid molecule, such as a disease-associated nucleic acid molecule, may be used in accordance with the methods of the invention, particularly such well-known methods as PCR, electrophoresis, Southern blotting, Northern blotting, Western blotting and ELISA. Standard methods for carrying out such detection techniques will be familiar to one of ordinary skill in the art.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Analysis of Molecular Models of Proteinase K

In one series of embodiments, polymer derivatives of Proteinase K are provided. Proteinase K from *Tritirachium album* has eight lysine residues (Gunkel, F. A., et al., (1989) Eur J Biochem 179:185–194), of which we have found six to be located on the solvent-accessible surface of the enzyme. The linear polymers used in certain embodiments can have a methoxy group or other unreactive group at one end of the polymer (referred to herein as an "unreactive polymer") and an electrophilic group at the other end. The latter groups can react to form covalent bonds with the alpha amino group of the amino-terminal alanine residue and with the epsilon amino groups of the accessible lysine residues.

Figure 1B:
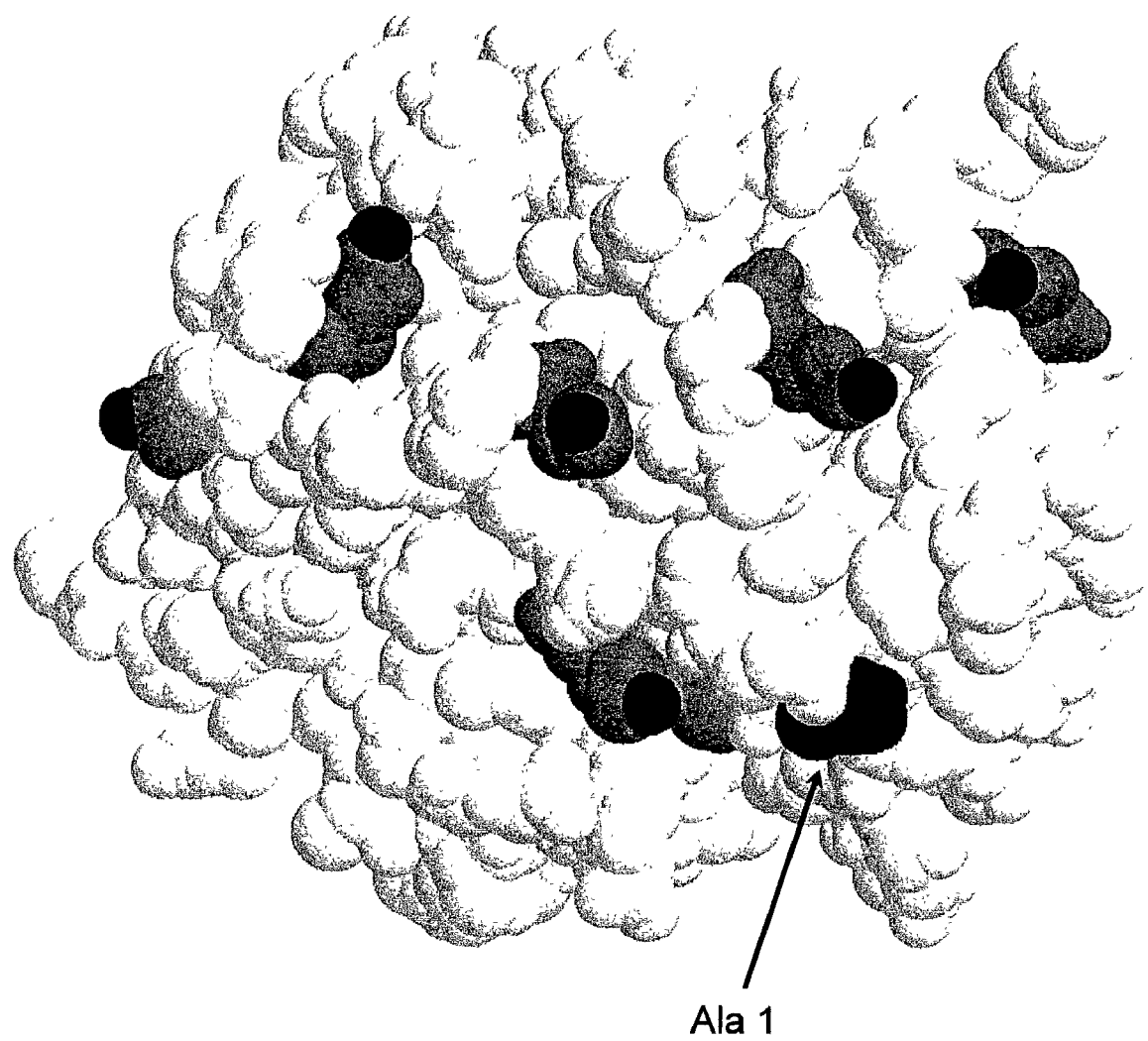
Figure 1C:
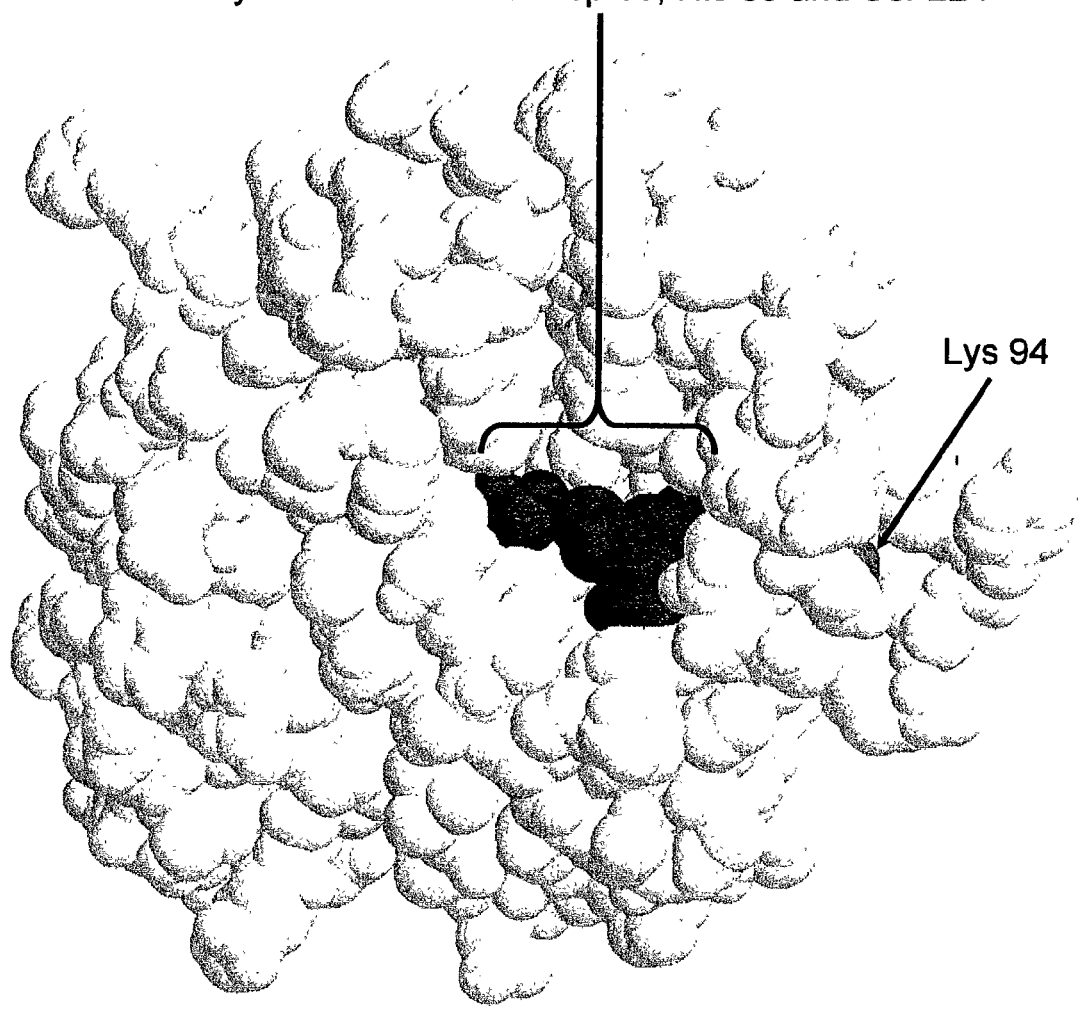

FIGS. 1a–1c depict three computer-generated images of the surface of Proteinase K. The structure was derived from x-ray crystallographic studies performed at the Institut für Kristallographie in Berlin (Wolf, W. M., et al., (1991) J Biol Chem 266:17695–17699; Müller, A., et al., (1994) J Biol Chem 269:23108–23111). The data from these studies were recorded in the Protein Data Bank ("PDB"), Research Collaboratory for Structural Bioinformatics under PDB Codes: 2PRK and 3PRK (see the internet website of Research Collaboratory for Structural Bioinformatics at .rcsb.org/pdb/ and Bhat, T. N., et al., (2001) Nucleic Acids Res 29:214–218). The x-ray coordinates were downloaded into RasMol Version 2.6 Beta 2 (Sayle, R. A., et al., supra) and a three-dimensional representation of the solvent-accessible surface of Proteinase K was displayed in which we have highlighted the amino-terminal and lysine residues.

FIG. 1a shows a representation of Proteinase K in which the surface containing the accessible lysines (herein labeled the "PEG Attachment Face") is seen to be clearly separated from the catalytic site (which is also visible in FIG. 1c). We have colored the lysine residues light gray and the nitrogen atoms of their epsilon amino groups black.

FIG. 1b shows one surface of Proteinase K that contains the six solvent-accessible lysine residues (Lys 57, 87, 118, 125, 242 and 258), which we have colored light gray. As in FIG. 1a, we have colored the nitrogen atoms of their epsilon amino groups, to which electrophilic derivatives of polymers such as PEG or PEO can attach, black, and the amino-terminal alanine (Ala 1) dark gray.

FIG. 1c shows a view of the surface of Proteinase K that reveals the catalytic site (which we have colored dark gray) and a portion of one of the poorly accessible lysine residues (Lys 94; Lys 86 is not shown). The "catalytic triad," identified by Müller, A., et al., supra, consists of one residue each of aspartic acid (Asp 29), histidine (His 69) and serine (Ser 224). These amino acid residues are located within the cleft where the scissile domain of the substrate protein can be bound. Their concerted interactions with the substrate promote its cleavage.

On the basis of these analyses of its molecular structure, we predicted that Proteinase K could be coupled to polymers on its amino-terminal alanine and on at least six lysine residues (Lys 57, 87, 118, 125, 242 and 258), without greatly diminishing its proteolytic activity. The data in FIG. 8, particularly for the conjugate with a mean of 6.3 PEGs per molecule of Proteinase K, are consistent with this prediction.

Example 2

Purification of Proteinase K and Polymer Coupling

Proteinase K (EC 3.4.21.64) from *Tritirachium album* was obtained from four sources: Worthington Biochemical Corporation, Lakewood, N.J. (catalog # PROK), Sigma Chemical Company, St. Louis, Mo. (catalog # P 2308), Amresco, Solon, Ohio (catalog # E195) and Roche, Indianapolis, Ind. (catalog # 1 373 200). In one experiment, 33 mg of Proteinase K powder (Sigma) was dissolved in 1 mL of Acetate Buffer A (5 mM sodium acetate, 5 mM acetic acid, pH 4.6) and loaded onto a Toyopearl MD-P SP sulfopropyl cation-exchange column (8.5 cm×7.5 mm) from TosoHaas (Montgomeryville, Pa.; catalog # 22223). After a 5-mL wash with Acetate Buffer A, the proteins were eluted with a 25-mL linear gradient of 0 to 300 mM NaCl in Acetate Buffer A, at a flow rate of 0.5 mL/min. Fractions of 2 mL were collected.

Aliquots of the fractions from the sulfopropyl column were assayed for proteolytic activity, i.e., the ability to digest casein into fragments that remain in the supernatant after precipitation of the intact protein and large polypeptides with trichloroacetic acid ("TCA"). Aliquots of the fractions were also analyzed by size-exclusion HPLC on a Superdex 75 10/30 column from Amersham Pharmacia Biotech (Piscataway, N.J.; catalog # 17-1047-01). Fractions 11 and 12 from the sulfopropyl column, which were eluted between 15.8 and 19.8 mL of the NaCl gradient, contained most of the proteolytic activity and a total of about 13 mg of protein (in 4 mL). The latter two fractions were combined and used as the substrate for the polymer coupling reactions described below.

A solution of Tris base (1 M) was prepared by dissolving 145 mg of Tris base (Sigma, catalog # T 1503) in 1.2 mL of water. Solutions of 0.1, 0.35 and 0.6 M Tris were prepared from the 1 M stock solution by dilution with water. Three solutions of PEG in 1 mM HCl, each containing a different type of "activated" PEG, were prepared as follows:

1) 25.6 mg of 2-kDa SPA-PEG [methoxypoly(ethylene glycol) N-succinimidyl propionate] from Shearwater Corporation (Huntsville, Ala.; catalog # 2M4M0D01) was dissolved in 0.33 mL of 1 mM HCl, giving a total volume of approximately 0.35 mL.
2) 64 mg of 5-kDa SPA-PEG from Fluka (Milwaukee, Wis.; catalog # 85969) was dissolved in 0.3 mL of 1 mM HCl (total volume=approximately 0.35 mL).
3) 64 mg of 5-kDa-NPC-PEG [methoxypoly(ethylene glycol) p-nitrophenyl carbonate] from Shearwater Corporation (catalog # 2M3B0H01) was dissolved in 0.3 mL of 1 mM HCl (total volume=approximately 0.35 mL).

Two minutes after dissolution, 0.2 mL of each of these solutions of activated PEG was added to a 0.16-mL portion of the purified Proteinase K pool (fractions 11 and 12 from the cation-exchange column). The addition of 0.04 mL of 1 M Tris base gave reaction mixtures with a volume of 0.4 mL, a pH of 8.3–8.4 and final concentrations of the respective activated PEGs of approximately 18 mM. This concentration is referred to as "4×" in the following text and the figures. Two-fold and four-fold dilutions in 1 mM HCl of portions of the 4× stock solutions of each type of activated PEG were combined with aliquots of the Proteinase K pool and with 0.04 mL of 0.6 M Tris or 0.04 mL of 0.35 M Tris, respectively, to produce reaction mixtures in which the final concentrations of activated PEG were approximately 9 mM and 4.5 mM, respectively, and the pH was 8.3–8.4. These are referred to below and in the figures as "2×" and "1×" PEG reaction mixtures, respectively.

One of the control reaction mixtures contained neither Tris base nor activated PEG and was prepared from 0.2 mL of water plus 0.16 mL of the Proteinase K pool and 0.04 mL of 1 mM HCl. Another control reaction mixture contained Tris base, but no PEG, and was prepared from 0.2 mL of 1 mM HCl plus 0.16 mL of the Proteinase K pool and 0.04 mL 0.1 M Tris base. Additional control reaction mixtures contained Tris and Acetate Buffer A, instead of Proteinase K, and final concentrations of 9 mM or 18 mM 5-kDa NPC-PEG. Thirty minutes after preparation, both of the latter solutions had pH values of approximately 9.2. After one day at 4–8° C., the pH had decreased to 8.6–8.7, as the NPC-PEG was hydrolyzed.

All of the reaction mixtures were incubated in a refrigerator at 4–8° C. After 19 hours of incubation, each of the three reaction mixtures containing 4× PEG (2-kDa SPA-PEG, 5-kDa SPA-PEG and 5-kDa NPC-PEG) was fractionated on a Superdex 75 HR10/30 column in Acetate Buffer A containing 150 mM NaCl, from which most of the single peak of PEGylated protein was collected. After a total of two days of incubation, aliquots of the remaining reaction mixtures (containing 1× or 2× PEG) and aliquots of the partially purified conjugates prepared with 4× PEG were analyzed by size-exclusion HPLC in Acetate Buffer B (10 mM acetic acid, 10 mM sodium acetate, 150 mM NaCl). After a total of three days of incubation, the remainder of each of the reaction mixtures containing 1× or 2× PEG was fractionated on the same Superdex 75 column, from which most of the single PEG-protein peak in each reaction mixture was collected. The proteolytic activities of the PEG-protein conjugates that had been purified by size-exclusion chromatography were assayed using casein as the substrate, under the standardized conditions, as described under Methods of Analysis, above. One month later, aliquots of several of the PEG-protein conjugate preparations were reanalyzed by size-exclusion HPLC in Acetate Buffer B and the conjugates were found to be stable. Some of the purified preparations (from which the unconjugated PEG had been removed) were also analyzed by polyacrylamide gel electrophoresis, as described in Example 4.

Example 3

Purification of Proteinase K and Coupling of PEG Aldehyde

In a similar manner, 61.2 mg of Proteinase K solution in 4 mL 10 mM pH 7.5 Tris-HCl buffer (Roche 1 373 200) was loaded onto a Toyopearl MD-P SP sulfopropyl cation-exchange column (8.5 cm×7.5 mm) from TosoHaas (Montgomeryville, Pa.; catalog # 22223) that had been equilibrated with Acetate Buffer C (5 mM sodium acetate, 5 mM acetic acid, pH 4.6, containing 1 mM $CaCl_2$). After a 5-mL wash with Acetate Buffer C, the proteins were eluted with a 25-mL linear gradient of 0 to 300 mM NaCl in Acetate Buffer C, at a flow rate of 0.5 mL/min. Fractions of 1 mL were collected. The peak fraction from each of two such runs was pooled to give 2 mL of 10.6 mg/mL protein. The pH of 1.71 mL of this pool was adjusted to 5.6 by addition of 0.09 mL of an acetate-phosphate buffer stock (0.05 mL glacial acetic acid plus 2.4 mL 0.5 M $Na_2HPO_4$ +0.5 M $NaH_2PO_4$+1 M NaCl). A 0.4 mL portion was removed and 309 mg 5-kDa-mPEG-propionaldehyde from Fluka (Milwaukee, Wis.; catalog # 75936) was dissolved in the remaining 1.4 mL. Because of the volume contribution of the added PEG this brought the volume of the PEG-proteinase mixture to about 1.65 mL of about 30 mM PEG aldehyde. A 20 mM PEG reaction was prepared by mixing 0.6 mL 30 mM PEG-proteinase with 0.3 mL of the retained buffered proteinase and adding 0.05 mL 45 mM borane-pyridine (0.03 mL 8 M borane-pyridine, Aldrich catalog # 17,975-2, plus 0.3 mM acetonitrile plus 0.2 mL water). A 0.06 mL portion of the 45 mM borane-pyridine was added to the remaining 1.05 mL 30 mM PEG-proteinase mixture. The two reaction mixtures were refrigerated for 5 days. Excess PEG and reaction byproducts were removed from the PEG-protein by size-exclusion chromatography on the Superdex 75 HR10/ 30 column. Multiple runs of 0.25–0.3 mL reaction mixture were eluted with Acetate Buffer D (5 mM acetic acid, 5 mM sodium acetate, 150 mM NaCl, 1 mM $CaCl_2$) and the peak 2 mL fractions of each of the two reactions pooled (see FIG. 7 for representative runs of each reaction).

Example 4

Electrophoretic Analyses of Proteinases and PEG Conjugates Thereof in the Presence or Absence of a Proteinase Inhibitor FIGS. 2a–2d depict results of studies in which samples of subtilisin (Sigma catalog # P 5380), PEG-subtilisin (Sigma, catalog # P 1459), purified Proteinase K and PEG conjugates of Proteinase K were analyzed by SDS-PAGE. FIGS. 2a–2d show results from gels in which the proteins were stained for protein with SYPRO® Ruby Stain (Molecular Probes, Eugene, Oreg.; catalog # S-12000) and the PEGylated adducts and free PEG were stained for PEG using one volume of 20% (w/v) $BaCl_2$ in 1 N HCl, combined with four volumes of a solution containing 1% (w/v) KI and 0.4% (w/v) $I_2$. With the SYPRO stain, the gels were illuminated at 302 nm and photographed in a dark hood with a Kodak digital camera, using an Orange/Red visible light filter (Molecular Probes, catalog #S-6655). The digital images of the gels stained for protein and/or PEG were analyzed using ID Imaging Analysis software from Kodak (Rochester, N.Y.). The horizontal axes in FIGS. 2a–2d represent mobilities as percents of the mobilities of the dye front. The vertical axes represent the relative intensities of protein stain or PEG stain. The baseline values for the various lanes have been shifted vertically to clarify the presentation of the results.

Figure 2A:
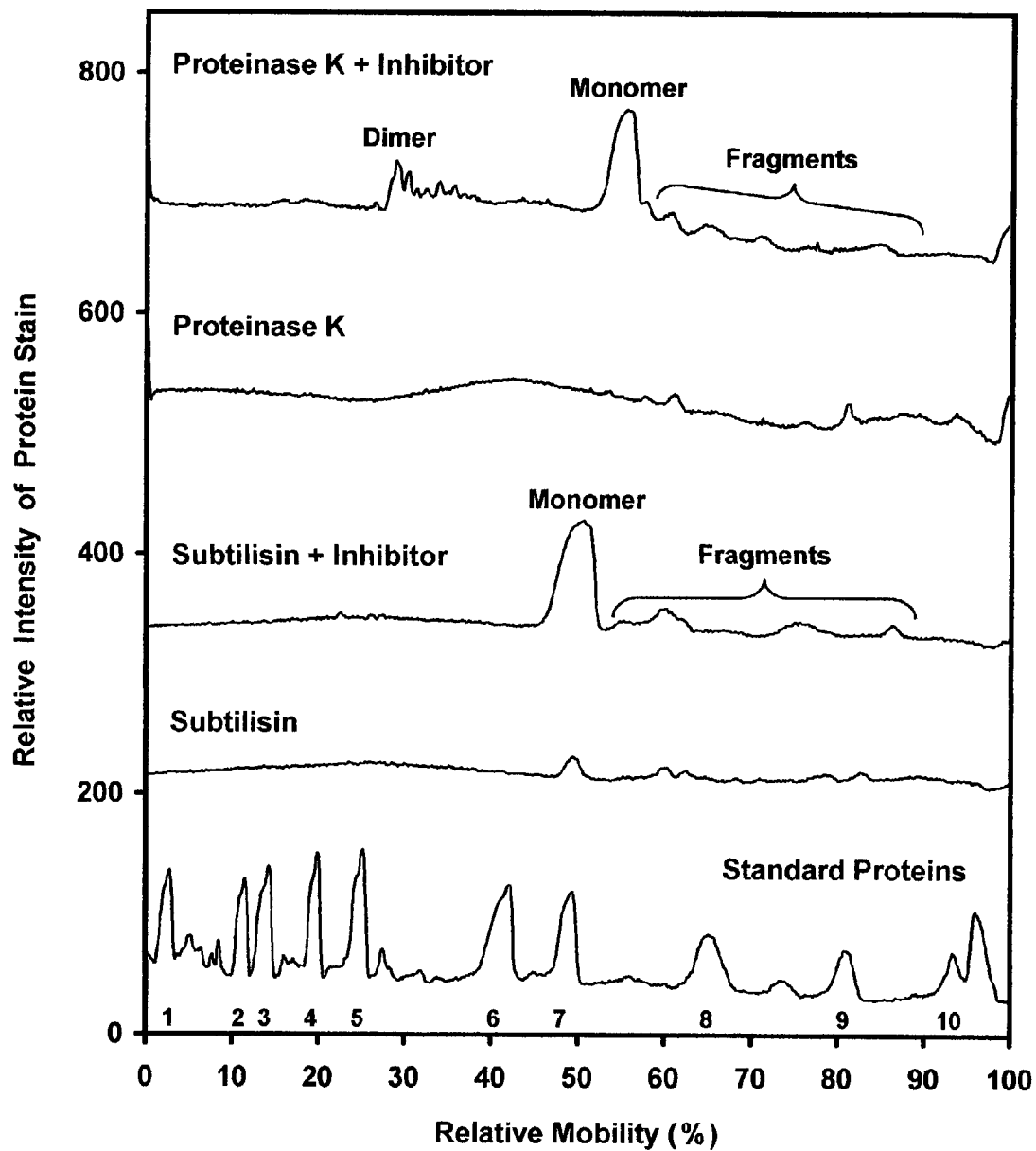
FIGS. 2a–2d depict results of gel electrophoretic analyses by polyacrylamide gel electrophoresis in the presence of SDS ("SDS-PAGE") of unmodified Proteinase K or subtilisin with or without the addition of a protease inhibitor prior to heating the proteinase samples with SDS (FIG. 2a); a commercial preparation of PEG-subtilisin electrophoresed with or without the addition of a protease inhibitor before heating the samples with SDS (FIG. 2b); and PEG conjugates of Proteinase K of this invention synthesized with two different concentrations of activated PEG (FIGS. 2c–2d). The gels were stained for protein only (2a and 2c), for both protein and PEG (2b) or for PEG only (2d). Digital photographs of the gels were analyzed quantitatively and the identities of the bands were established with reference to the mobilities of proteins and PEG-protein conjugates of known molecular weight.

FIG. 2a depicts results of studies in which Proteinase K and subtilisin were analyzed by SDS-PAGE after heating in a sample buffer containing SDS (Invitrogen, San Diego, Calif., catalog # NP0007) and a reducing agent (Invitrogen, catalog # NP0004), with or without the addition of the proteinase inhibitor 4-(2-aminoethyl)-benzenesulfonyl fluoride ("AEBSF") (Sigma, catalog # A8456) (see Mintz, G. R., (1993) BioPharm 6(2):34–38; Scott, M. R., et al., supra). The bottom tracing in FIG. 2a represents a mixture of standard proteins (Mark 12™ from Invitrogen, catalog # LC5677), in which the peaks numbered 1 through 10 are identified as proteins having the following molecular weights (all in kDa): 200, 116, 97.4, 66.3, 55.4, 36.5, 31.0, 21.5, 14.4 and 6. SDS-PAGE analysis of commercially available subtilisin (Sigma P-5380), from which most of the fragments had been removed by cation-exchange chromatography, revealed a single major peak (labeled Monomer) and small quantities of fragments or other minor contaminants of low molecular weight (second and third tracings from the bottom). Most of the fragments present in the subtilisin as received from Sigma were removed 1 day prior to electrophoretic analysis. The presence of some fragments in these analyses demonstrates the autolysis that occurs during storage. For subtilisin, the mobility of the major peak was found to correspond to a molecular weight of c. 31 kDa, by reference to a polynomial fit of data for the logarithm of the molecular weights of the standard proteins versus their mobilities relative to the dye front. For Proteinase K, the major peak corresponded to a molecular weight of c. 30 kDa.

The upper two tracings in FIG. 2a represent SDS-PAGE analyses of Proteinase K. The first and third tracings from the top of FIG. 2a represent samples of Proteinase K and subtilisin, respectively, where a final concentration of 20 mM AEBSF was added to the proteinases and incubated in 25 mM Tris base at room temperature for 20-minutes prior to the preparation of the samples for gel electrophoresis by heating in the presence of SDS. The very low intensity of protein stain found in the second and fourth tracings from the top (samples without protease inhibitor) confirms the benefit of including the inhibitor during the preparation of samples for electrophoretic analysis of these proteinases.

Figure 2B:
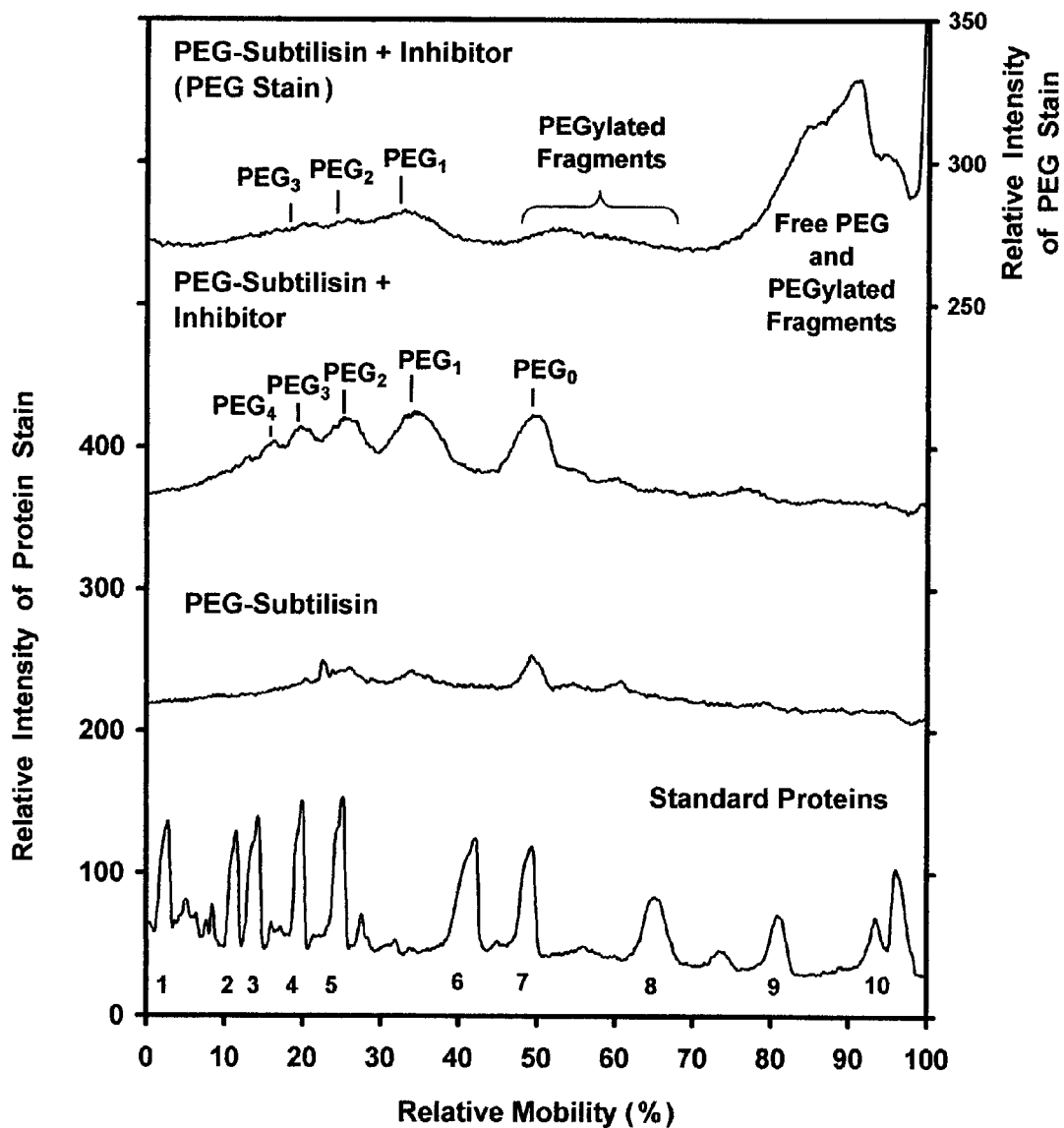

FIG. 2b depicts the results of SDS-PAGE analysis of commercially available PEG-subtilisin (Sigma, catalog # P 1459), with and without the addition of AEBSF prior to preparation of the samples for electrophoresis. Staining for PEG (upper tracing) reveals a predominance of PEG in the low molecular weight region (characteristic of free PEG and PEGylated small fragments of protein) and a modal PEGylated protein species with only one PEG per protein molecule. Protein staining (second and third tracings from the top) reveals the presence of a substantial quantity of unPEGylated protein (labeled $PEG_0$ in the figure) and confirms the inference from PEG staining that the monoPEGylated form of PEG-subtilisin predominates in this preparation. The relatively weak intensity of protein staining in the third tracing from the top (without AEBSF), in contrast with the second tracing from the top (with AEBSF), confirms the benefit of adding an inhibitor of proteinase activity prior to preparation of samples for SDS-PAGE analysis of such PEG-proteinase conjugates.

Figure 2C:
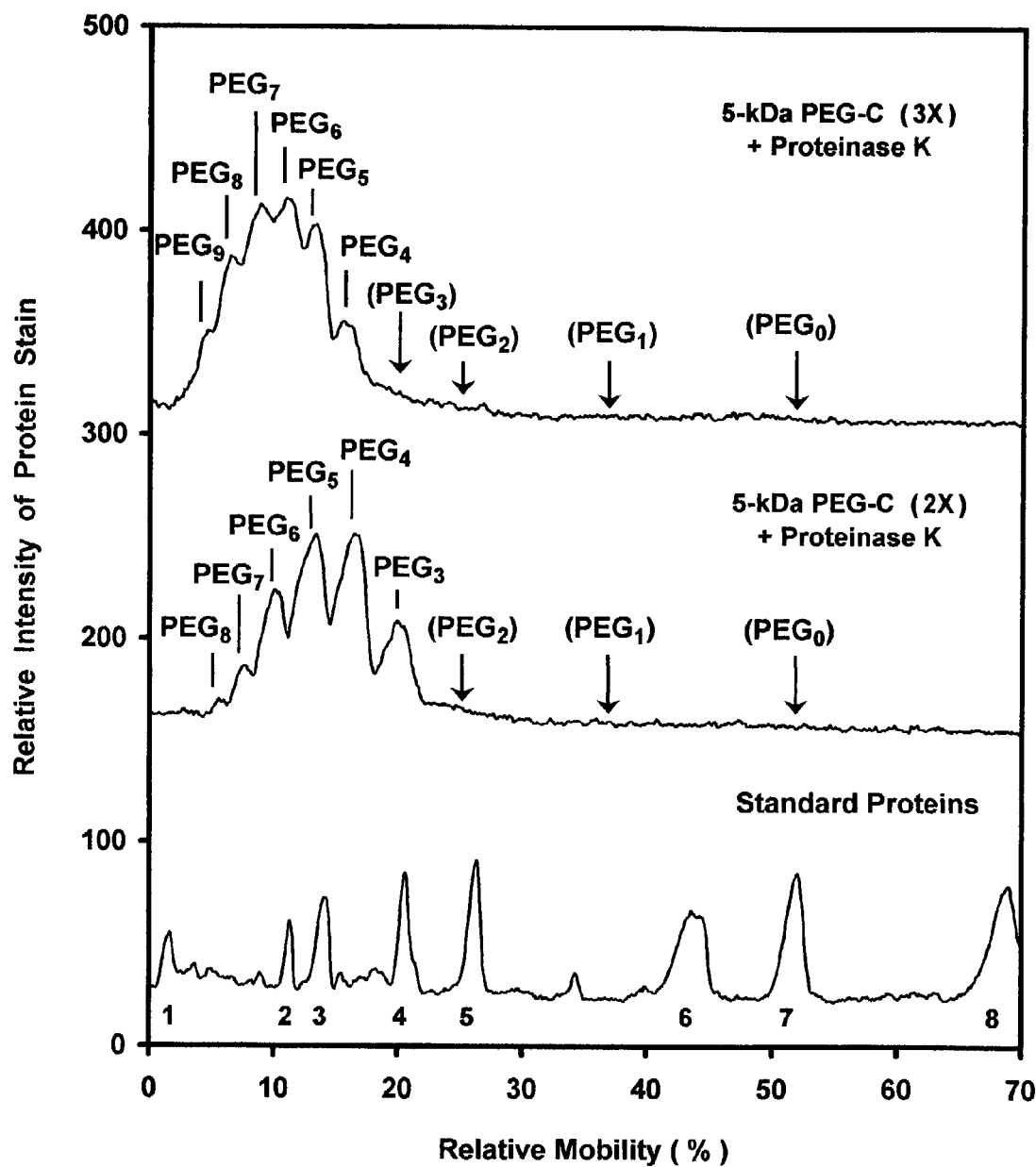
Figure 2D:
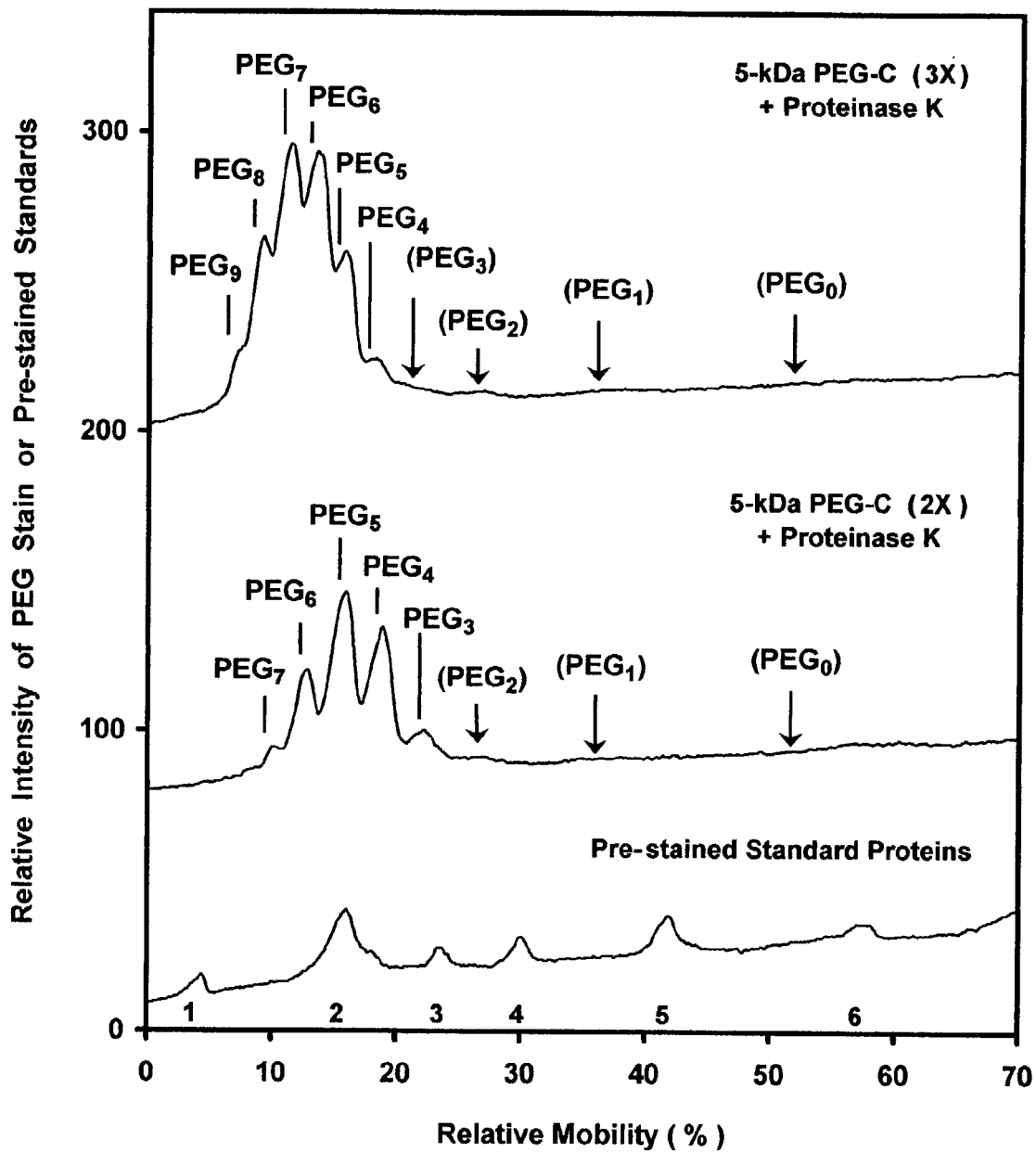

FIGS. 2c and 2d depict electrophoretic analyses of the products of reacting Proteinase K with 20 mM PEG aldehyde ("PEG-C (2×)") or 30 mM PEG aldehyde ("PEG-C (3×)"). In both of the PEGylated samples, the free PEG was removed prior to electrophoresis by size-exclusion chromatography. The tracings depict the intensities of the bands in a digital photograph of the gel stained for protein (FIG. 2c) and the gel stained for PEG (FIG. 2d) that were analyzed quantitatively using Kodak Imaging software, as described for the gel in FIGS. 2a and 2b. The bottom tracing in FIG. 2c shows Mark 12™ protein standards, as described in FIG. 2a, and the bottom tracing in FIG. 2d shows results obtained for pre-stained standard proteins (SeeBlue Plus2™, Invitrogen catalog # LC5625), in which the peaks numbered 1 through 6 identify proteins with the following apparent molecular weights (in kDa): 204, 111, 68.8, 51.5, 40.2 and 28.9 kDa. The gels were also calibrated by performing similar analyses of PEGylated preparations of carbonic anhydrase (Sigma, catalog # C 2522), a stable enzyme that has approximately the same molecular weight as Proteinase K and is not subject to autolysis. Comparison of the results for PEGylated Proteinase K with the results for PEGylated carbonic anhydrase (not shown), enabled the identification of conjugates of Proteinase K containing three strands of PEG ("$PEG_3$") through eight strands of PEG ("$PEG_8$;" second tracing from the bottom). Similar analysis of the PEG-Proteinase K that contained 30 mM PEG in the reaction mixture revealed a mixture of conjugates, some of which contained as many as nine strands of PEG (top tracing).

Example 5

Characterization of a Newly-synthesized PEG Aldehyde Conjugate of Subtilisin Carlsberg and a Commercially Available PEG-Subtilisin Thirty milligrams of subtilisin Carlsberg (Sigma, catalog # P 5380) was dissolved in 1 mL of Acetate Buffer A (5 mM sodium acetate, 5 mM acetic acid, pH 4.6) and 0.09 mL loaded onto a Superdex® 75 10/30 size exclusion column (Amersham Pharmacia Biotech, Piscataway, N.J.; # 17-1047-01), with Acetate Buffer D (5 mM sodium acetate, 5 mM acetic acid, containing 1 mM $CaCl_2$ and 150 mM NaCl) as the running buffer and a 0.5 mL/min flow. The eluate between 25.2 and 27.0 minutes (the subtilisin monomer peak) from three such runs was collected and pooled together (approximately 0.6 mg/mL).

The pH of 1.7 mL of this pool was adjusted to 5.8 by the addition of 0.18 mL of acetate-phosphate buffer (0.05 mL glacial acetic acid plus 2.4 mL 0.5 M $Na_2HPO_4$+0.5 M $NaH_2PO_4$+1 M NaCl). A 0.21 mL portion was removed and 328.5 mg of 5-kDa-mPEG-propionaldehyde from Fluka (Milwaukee, Wis.; catalog #75936) was dissolved in the remaining 1.49 mL. Because of the volume contribution of the added PEG, this brought the volume of the mixture of PEG and subtilisin to 1.75 mL and the concentration of PEG aldehyde to 38 mM. The reaction mixture was completed by adding 0.1 mL of 45 mM borane-pyridine (0.03 mL 8 M borane-pyridine, Aldrich catalog #17,975-2, plus 0.3 mM acetonitrile plus 0.2 mL water) and incubating the sample at 4–8° C.

After 6 days, the reaction mixture was analyzed by size exclusion HPLC on a Superdex® 200 10/30 column (Amersham Pharmacia Biotech, Piscataway, N.J.; #17-1088-01) in Acetate Buffer B (10 mM acetic acid, 10 mM sodium acetate, 150 mM NaCl) to determine the extent of PEGylation. Also analyzed at the same time was a commercially available PEG-subtilisin Carlsberg conjugate (Sigma, catalog #P1459). This sample was freshly made by dissolving Sigma's PEG-subtilisin in Acetate Buffer B (2 mg in bottle+1 mL buffer). Sigma's PEG-subtilisin is labeled as having 6 moles of PEG per mole of protein. However, FIG. 3 displaying the HPLC chromatogram of Sigma's product (top tracing) shows a peak distribution of 1–2 PEGs attached per subtilisin molecule. Results from SDS-PAGE of Sigma's product are also available in FIG. 2b (top two tracings) and show an average of 1.5 PEG strands attached per subtilisin. The bottom tracing in FIG. 3 shows the PEG-subtilisin of this invention has an average of 5 PEGs attached per subtilisin. The peak that has a retention time of c. 24 minutes is inferred to be a condensation product of two molecules of PEG aldehyde, of which the apparent molecular weight is 10 kDa. This byproduct can be readily separated from the PEG-subtilisin by art-known chromatographic methods.

Example 6

Stability of Proteinase K and its PEG Conjugates During Prolonged Heating

Figure 4:
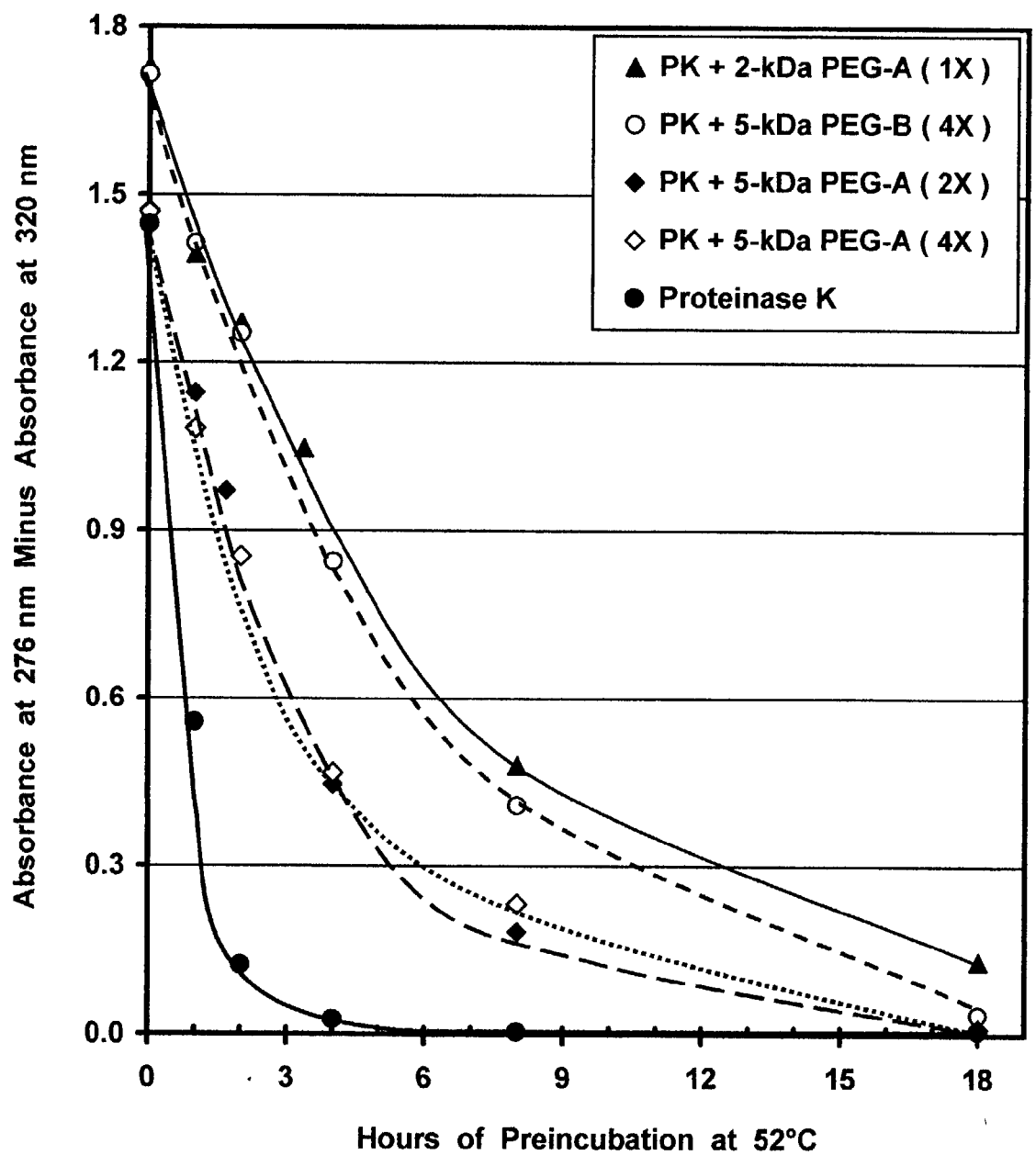
FIG. 4 shows graphs of the residual proteolytic activities of the initial, unmodified Proteinase K and several PEG conjugates thereof, following incubation for up to 18 hours at 52° C.

FIG. 4 depicts the residual proteolytic activity after various periods of heating (up to 18 hours) of Proteinase K and four polymer-stabilized conjugates of this invention. Four PEG conjugates of Proteinase K that were found to be significantly stabilized during a preliminary 90-minute experiment were assayed in this longer-term study. In FIG. 4, Proteinase K activity is expressed as the absorbance at 276 nm of centrifugally clarified supernatants after precipitation of the undigested casein and large polypeptides by trichloroacetic acid ("TCA"). The absorbance data were partially corrected for light scattering by subtracting the absorbance at 320 nm. For the initial, unmodified Proteinase K (filled circles), the activity decreased rapidly during heat pre-treatment. After 1 hour at 52° C., the activity had decreased to less than 50% of the initial value, and after 2 hours at 52° C., it had decreased to less than 10%. Thereafter, the activity continued to decrease, and by 4 hours, it was nearly undetectable. After 8 hours or 18 hours at 52° C., no caseinolytic activity could be measured in the initial, unmodified Proteinase K.

FIG. 4 also shows the effects of heat pre-treatment on the proteolytic activity of four PEG conjugates of Proteinase K. The conjugate that was synthesized using 4.5 mM 2-kDa SPA-PEG ("PEG-A (1×)") during the coupling reaction (filled triangles) was initially more active than the unmodified Proteinase K (filled circles) and retained significant catalytic activity at all time points, including 18 hours. The conjugate that was synthesized using 18 mM 5-kDa NPC-PEG (open circles; "PEG-B (4×)") showed a similar pattern of residual proteolytic activity to that obtained with 4.5 mM 2-kDa SPA-PEG, except after 18 hours. Prior to exposure to heat, the conjugates that were synthesized using either 18 mM 5-kDa SPA-PEG (open diamonds) or 9 mM 5-kDa SPA-PEG (filled diamonds) showed similar initial activity to that of unmodified Proteinase K, but they were inactivated more slowly during heating. These results show that the Proteinase K conjugates of this invention exhibited partial loss of activity during incubation at 52° C. in the absence of the substrate (casein), but the rates of their inactivation were substantially slower than for unmodified Proteinase K.

Figure 5:
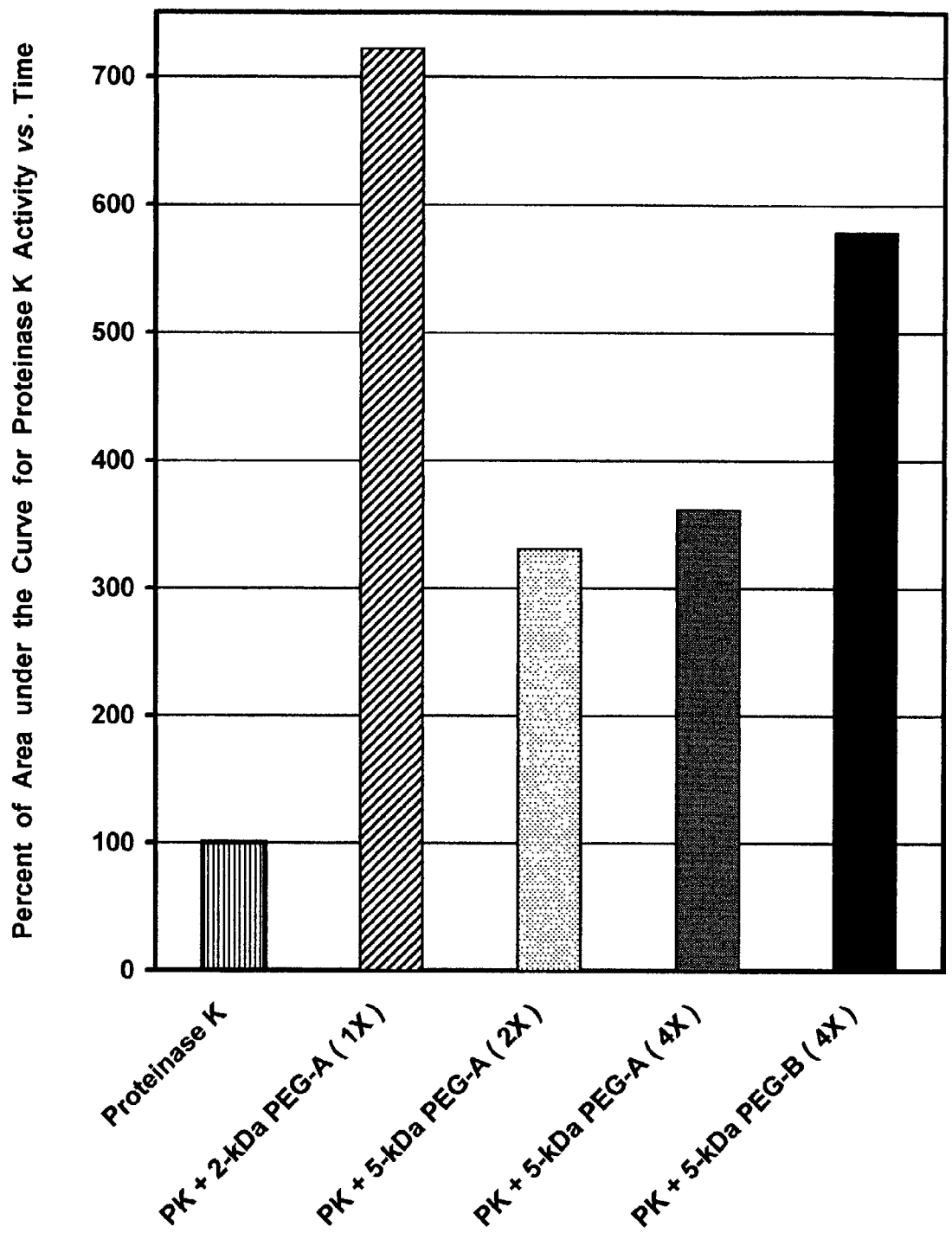
FIG. 5 summarizes the data for the areas under the curves ("AUCs") for the residual proteolytic activities (i.e., "integrated enzymatic activities") of the initial Proteinase K and various PEG-proteinase conjugates as a function of the time of preincubation at 52° C., based on the data in FIG. 4.

FIG. 5 depicts a summary of results of the activity assays depicted in FIG. 4, in which the vertical axis is proportional to the total area under the curve ("AUC") for each enzyme preparation during 18 hours. As a basis for comparison of the results obtained with the four PEG conjugates, the AUC of unmodified Proteinase K was defined as 100%. The Proteinase K conjugate synthesized with 4.5 mM 2-kDa SPA-PEG (diagonally hatched bar) had more than seven times the integrated activity of the initial, unmodified Proteinase K (vertically striped bar), integrated over the 18 hours of the experiment. During this time period, the other PEG derivatives of Proteinase K (lighter and darker stippled bars and black bar) had approximately three or approximately six times greater integrated activity than did the initial, unmodified Proteinase K.

Example 7

Effect of pH on the Stability of Proteinase K to Heat

In order to avoid additional variables in studies of the effect of pH on the stability of this enzyme, a composite buffer solution ("GTT buffer") was prepared that provided good buffering over a range of pH values from 7 to 10. Under the conditions of the preincubation at 52° C., the final concentrations of glycine, N-tris(hydroxymethyl)methyl)-2-aminoethane sulfonic acid ("TES") and tris(hydroxymethyl) aminomethane ("Tris") were each 32 mM. This buffer, titrated to various pH values, was used to obtain the results in FIG. 6a. As expected from the reported pH optimum of Proteinase K, which is in the range of pH 9–11 (U.S. Pat. No. 5,278,062), the enzyme was most stable to heat at pH 7, and least stable at pH 9.5, among the conditions tested in the experiments shown in FIG. 6a.

Figure 6A:
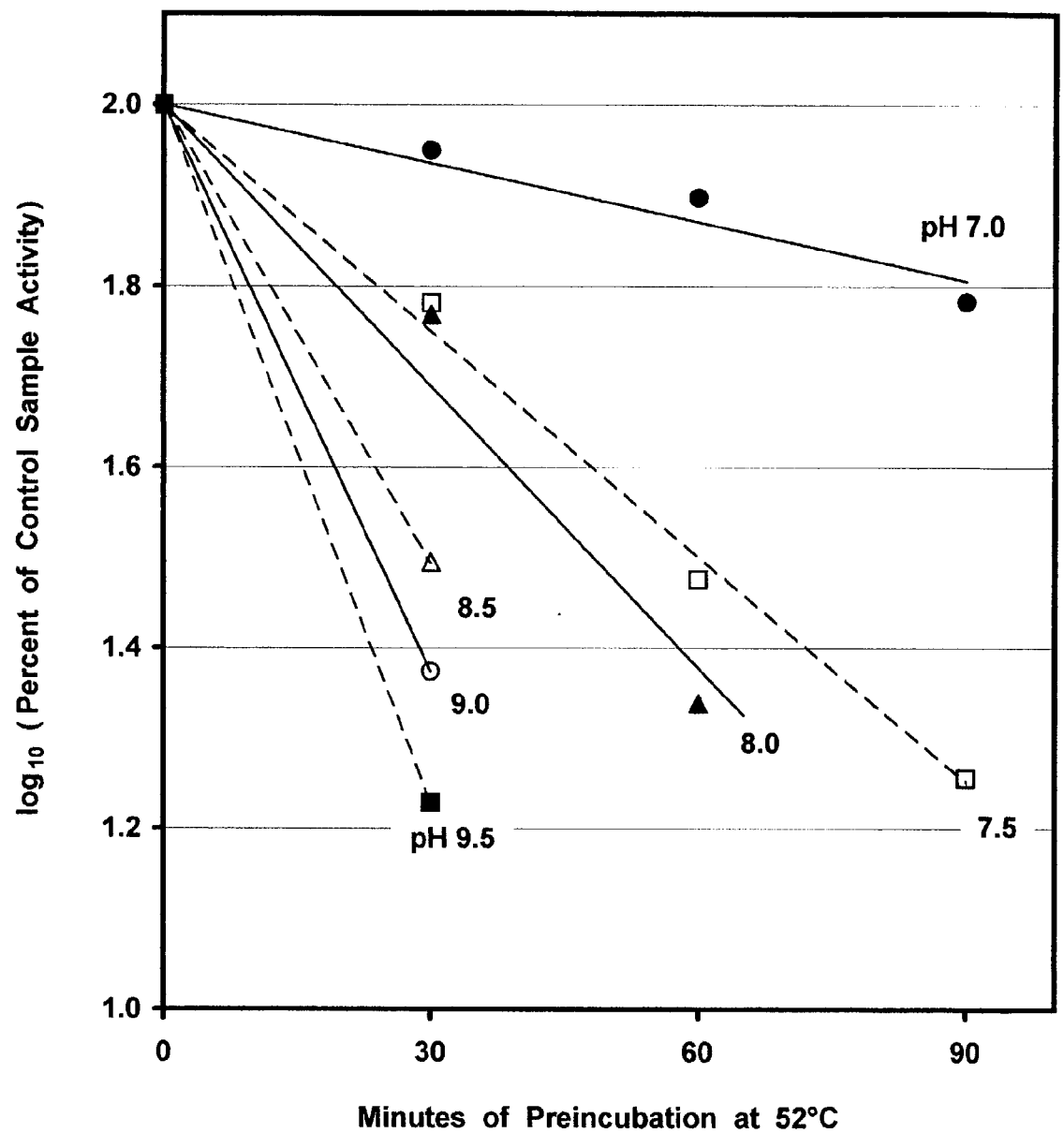
FIGS. 6a and 6b illustrate the effects of pH, heat, the addition of unreactive monomethoxyPEG ("mPEG") and/or conjugation of PEG on the stability of Proteinase K during preincubation for up to 90 minutes at 52° C.
Figure 6B:
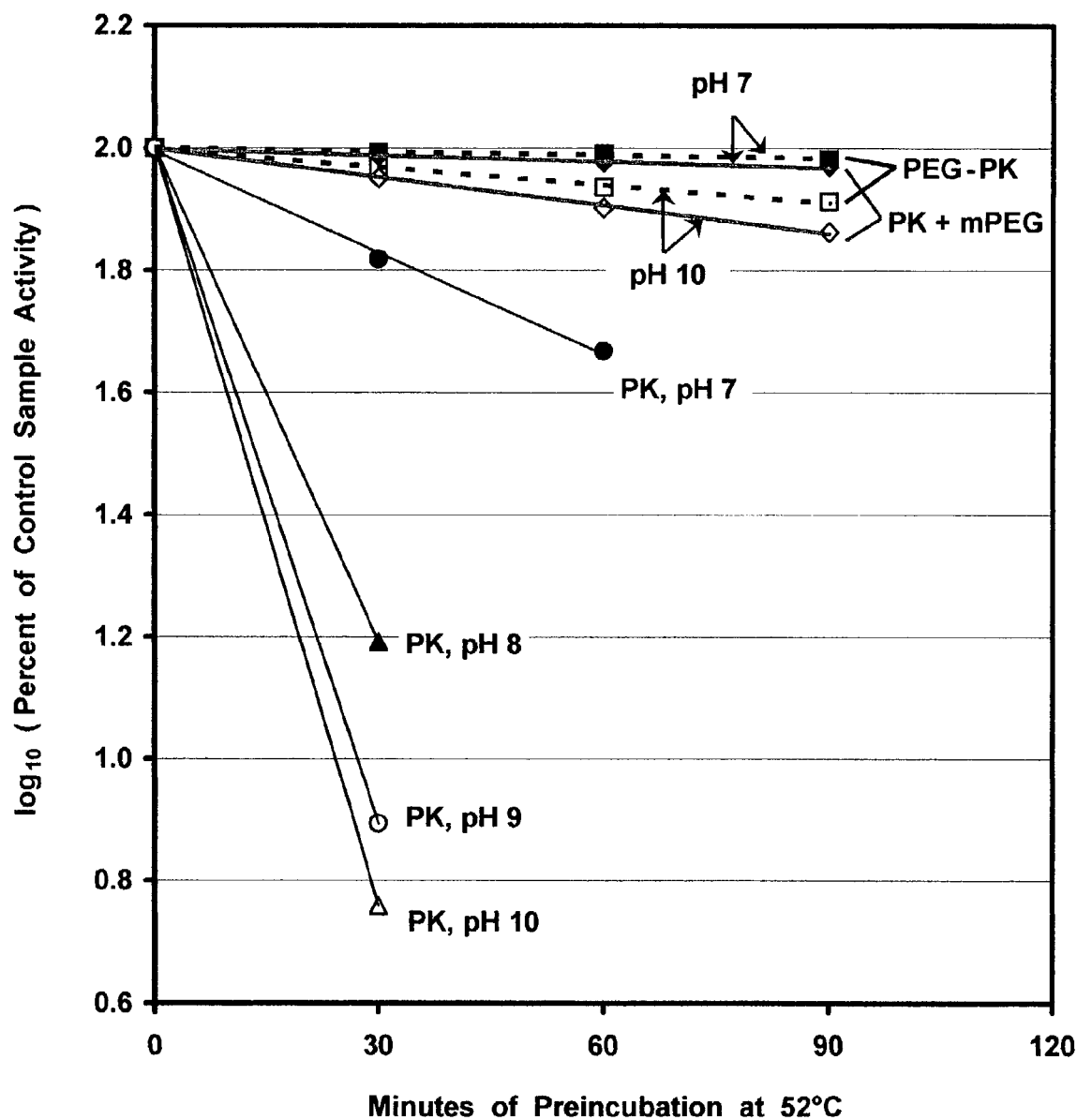

In FIGS. 6a and 6b, the vertical axis represents the logarithm of the residual Proteinase K activity, expressed as a percentage of that of the initial, unmodified Proteinase K without preincubation. The horizontal axis represents the time of incubation at 52° C.

From the results in FIGS. 4–6, we conclude that exposure to heat in the absence of denaturants or in the presence of SDS, guanidinium salts or urea can rapidly decrease the catalytic activity of Proteinase K, and that optimized coupling to PEG or, to a lesser extent, admixture with PEG can substantially protect Proteinase K from the loss of activity during exposure to heat and/or chaotropic agents. Therefore, the PEG conjugates and compositions of this invention exhibit desirably increased stability under the harsh conditions that can be used for nucleic acid extraction and isolation, particularly in robotic applications.

Example 8

Figure 7:
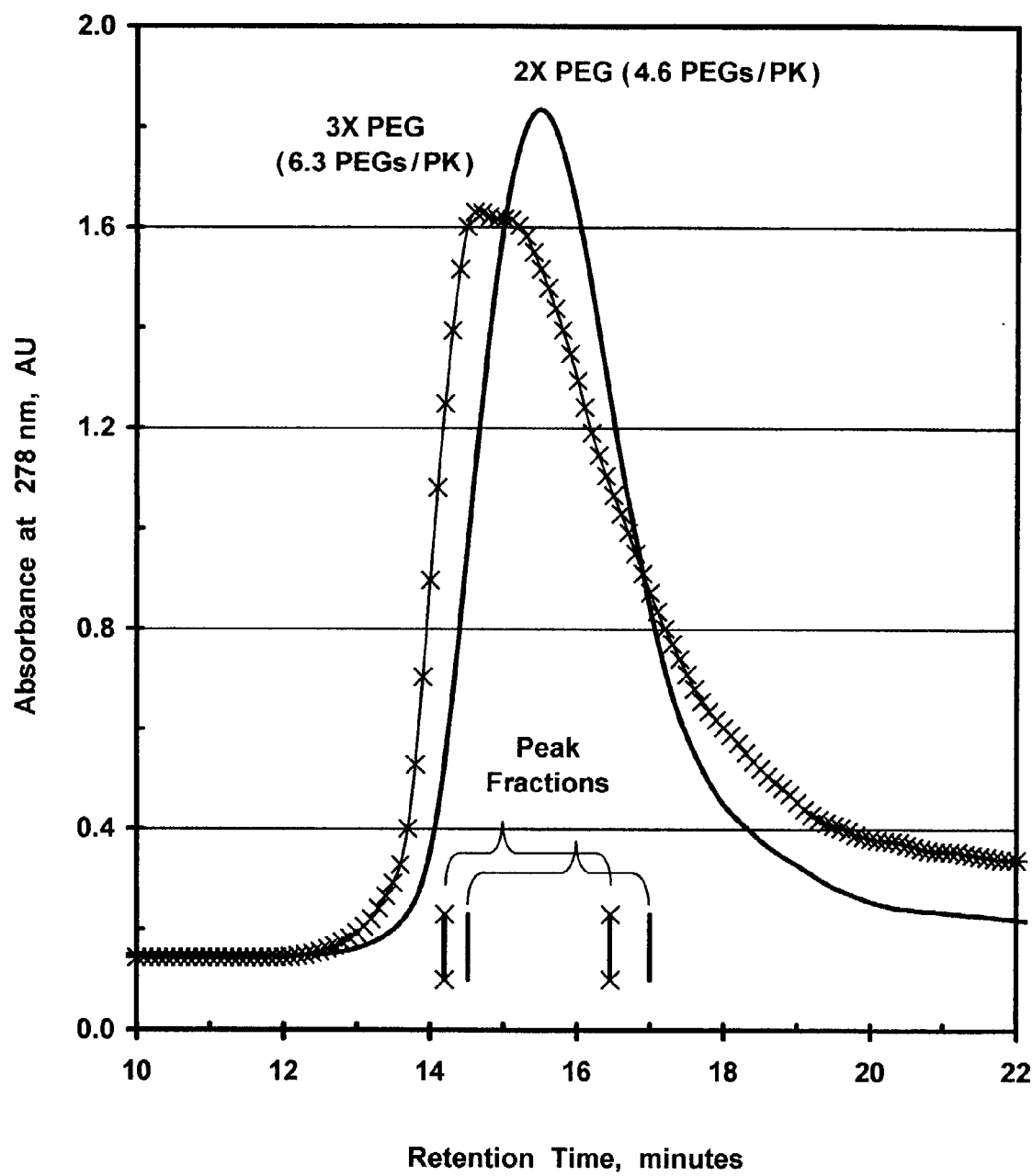
FIG. 7 depicts results of size-exclusion chromatography of two preparations of PEGylated proteinase K, in which the mean numbers of strands of PEG per enzyme molecule determined by SDS-PAGE analysis were approximately 4.6 and 6.3 in the peak fractions.
Figure 8:
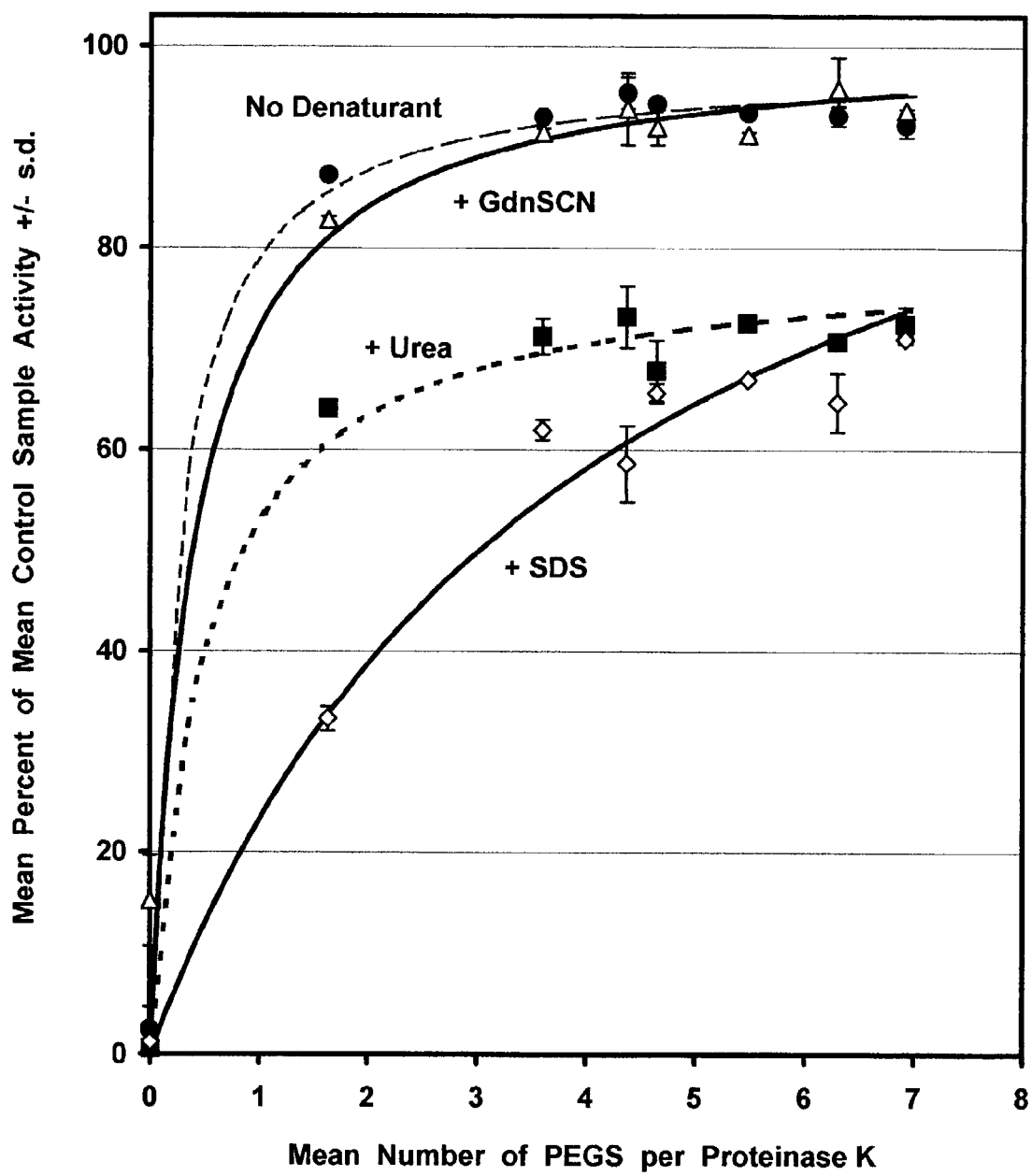
FIG. 8 depicts the residual proteolytic activities of purified Proteinase K and conjugates containing various numbers of strands of PEG, following preincubation for 2 hours at 52° C. in the absence of denaturants or the presence of 0.1 M GdnSCN, 2 M urea or 0.5% SDS. The conjugates were synthesized using two different coupling chemistries. The p-nitrophenyl-carbonate derivative of monomethoxy PEG (NPC-PEG) is referred to herein as "PEG-B." The propionaldehyde derivative of monomethoxy PEG is referred to herein as "PEG-C." The Schiff base formed by the aldehyde with amino groups on the protein was reduced to a secondary amine with pyridine borane, as used, e.g. in PCT publication WO 96/11953 (Kinstler, O. B., et al.). Proteolytic activities were measured under standardized conditions, with casein as the substrate, as described below under Methods of Analysis. The activity of the initial Proteinase K or conjugate that had not been preincubated was defined as 100%. The initial activities of the untreated conjugates ranged from 89% to 110% of that of untreated Proteinase K, with an average of 95±5% for the seven preparations incubated under the various conditions FIG. 9 summarizes the results of studies of the timecourse of the loss of activity of Proteinase K and a PEG-proteinase conjugate during heating at 52° C. in the absence of denaturants or the presence of 0.1 M GdnSCN or 2 M urea or 0.5% (w/v) SDS. The conjugate had a mean of 6.3 strands of PEG per proteinase molecule.

Stabilization of Proteinase K to Heat Inactivation in the Absence or Presence of Denaturants by PEGylation to Various Extents FIG. 7 illustrates representative size-exclusion chromatographic separations from the reactants and other products of Proteinase K PEGylated to two different extents. The mean number of strands of PEG per molecule of enzyme in each preparation was determined by quantitative SDS-PAGE, as in FIGS. 2a–2d. FIG. 8 depicts the dependence on the mean number of strands of 5-kDa PEG attached of the preservation of enzymatic activity during heating for 2 hours at 52° C. in the absence of denaturants (filled circles), the presence of 0.1 M guanidinium thiocyanate (open triangles), the presence of 2 M urea (filled squares) or the presence of 0.5% (w/v) sodium dodecyl sulfate (open diamonds). The conjugates used in this study were synthesized with 18 mM NPC-PEG (1.6 PEGs/monomer) or 36 mM NPC-PEG (3.6 PEGs/monomer) or with 20 mM PEG aldehyde (4.4, 4.6 and 5.5 PEGs/monomer) or 30 mM PEG aldehyde (6.3 and 6.9 PEGs/monomer). Free PEG was removed by size-exclusion chromatography on a Superdex 75 column in Acetate Buffer D, defined in Example 3. The mean number of strands of PEG for each sample was determined by quantitative analysis of photographs of electrophoretic gels stained for protein or PEG, as shown in FIGS. 2c and 2d. Representative results for the half-lives ($T_{1/2}$) are presented in Table 1 (FIG. 12).

Figure 9:
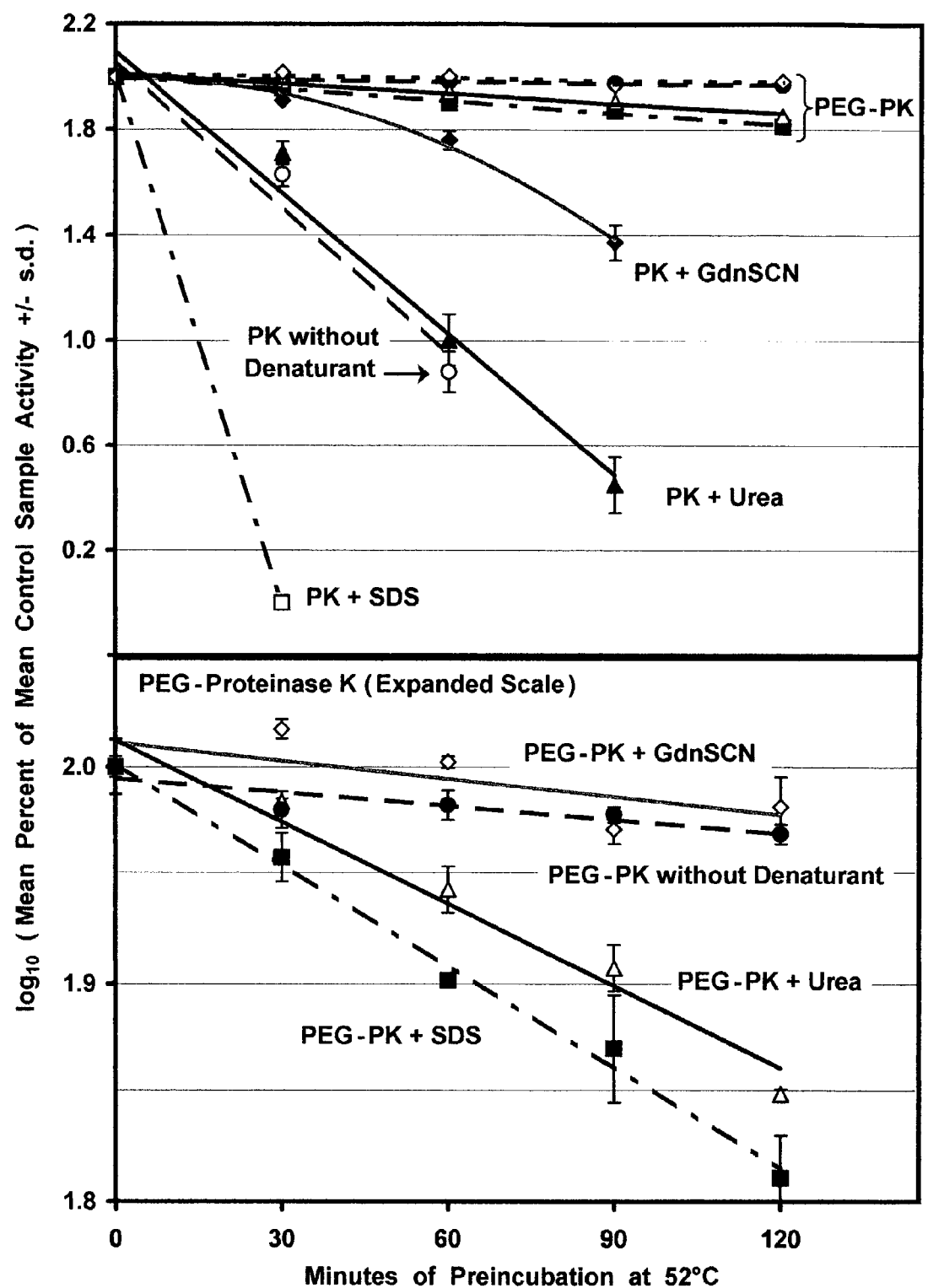

From the results in FIGS. 8 and 9 it is apparent that coupling as few as one strand of PEG confers increased stability; however, more than two strands of 5-kDa PEG must be coupled to achieve maximal stabilization under each of the tested conditions. Similar, nearly maximal extents of stabilization were provided by the coupling of an average of approximately four strands through seven strands of PEG. Semi-logarithmic plots of the inactivation rates at 52° C. of Proteinase K ("PK") and PEG-Proteinase K conjugates ("PEG-PK"), with and without the addition of 0.5% SDS, 2 M urea or 0.1 M GdnSCN are shown in FIG. 9. The half-lives of these first-order decay curves are summarized in Table 1 (FIG. 12). Among the tested denaturant solutions, the unmodified enzyme was most stable in 0.1 M GdnSCN ($T_{1/2}$=41 min), less stable in 2 M urea ($T_{1/2}$=17 min) and least stable in 0.5% SDS ($T_{1/2}$=7 min). The increases in half-life, relative to that of unmodified Proteinase K, of the conjugates with a mean of 1.6 to 6.3 strands of PEG were 11- to 14-fold in urea, 11- to 26-fold in GdnSCN and 11-to 27-fold in SDS (see Table 1 (FIG. 12)).

Example 9

Figure 10:
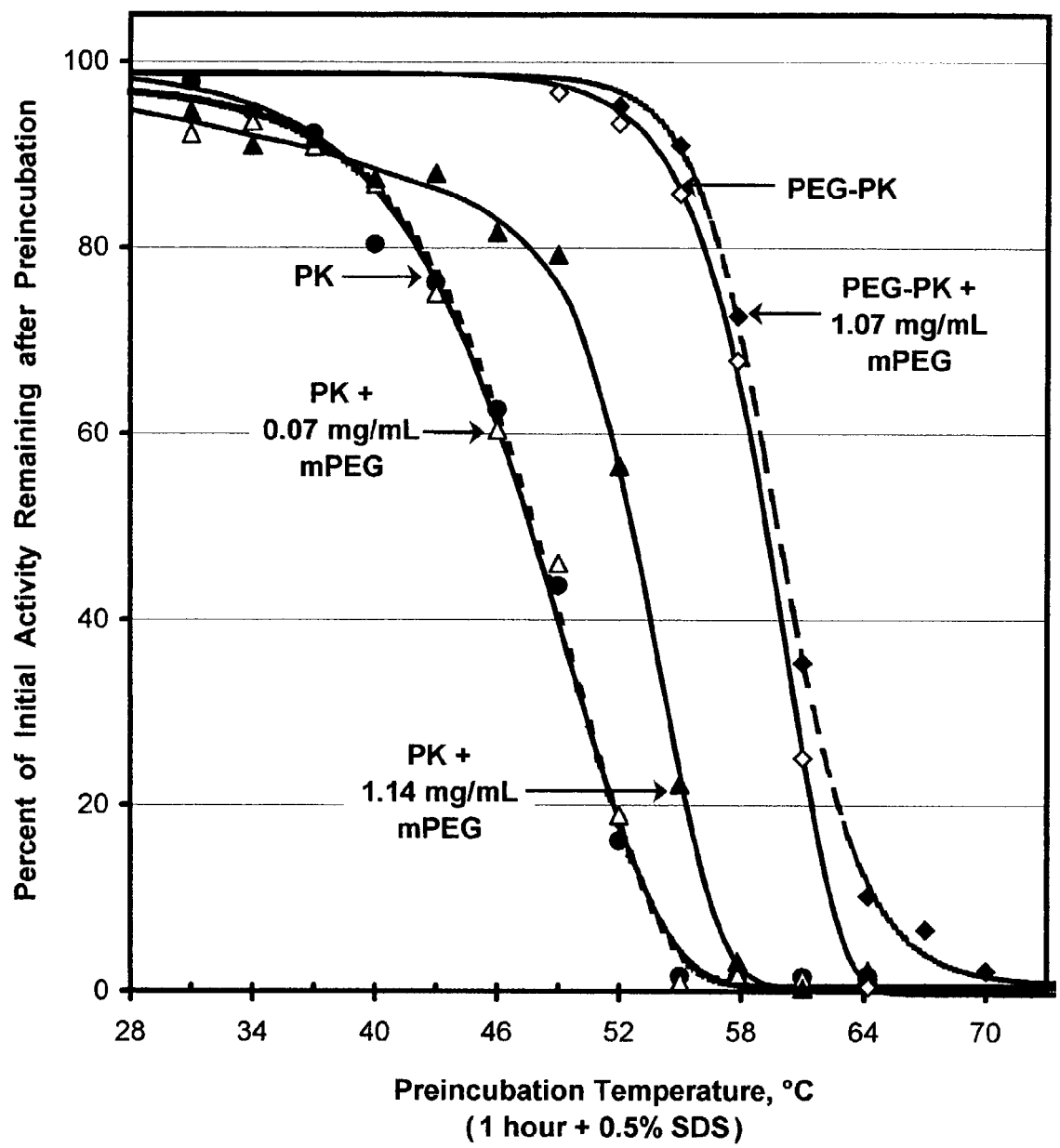
FIG. 10 shows the stabilizing effect of the addition of free mPEG on Proteinase K and on a PEG conjugate of Proteinase K incubated at a series of temperatures between about 30° C. and 70° C.

Stabilization of Proteinase K to Heat in the Presence of a Denaturant by PEGylation and/or the Addition of Free mPEG FIG. 10 depicts the residual proteolytic activity of purified Proteinase K and a conjugate of Proteinase K containing a mean of 6.3 strands of PEG, following preincubation for 1 hour with 0.5% sodium dodecyl sulfate (SDS) and the indicated amounts of free mPEG (from zero to 1.14 mg/mL). Preincubation was performed at temperatures ranging from 31° to 70° C. Following the preincubation, proteolytic activities were measured under standardized conditions with casein as the substrate, as described in Methods of Analysis. The activities of the samples that had not been preincubated were defined as 100%. FIG. 10 depicts the increased resistance to inactivation by heat in the presence of a detergent that results from coupling MPEG to Proteinase K, with or without the addition of free mPEG to the preincubation solution. The conjugate used in this study was synthesized by reductive alkylation with 30 mM PEG aldehyde and pryidine-borane. The preparation containing a mean of 6.3 strands of PEG per Proteinase K molecule was purified by size-exclusion chromatography as shown in FIG. 7. The indicated amounts of free mPEG were added to the preincubation solutions to determine the stabilizing effects of free mPEG on Proteinase K ("PK") and on the polymer-proteinase conjugate ("PEG-PK"). Mixing with free mPEG improved the stability of Proteinase K and of the polymer-proteinase conjugate, but the conjugate retained its increased resistance to inactivation relative to the unmodified enzyme at all of the tested concentrations of free MPEG (up to 12 mg/mL).

Figure 11:
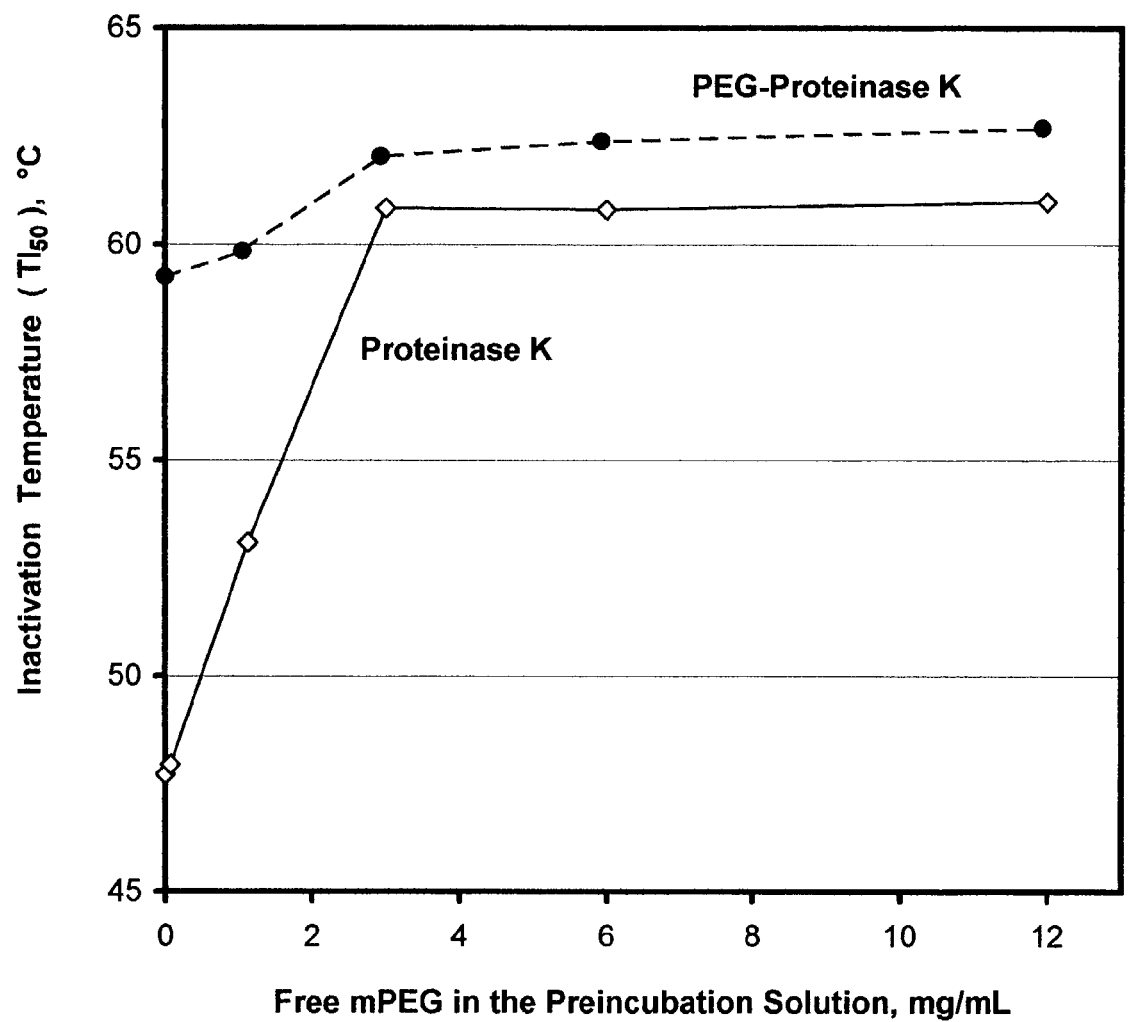
FIG. 11 shows the concentration dependence of the stabilizing effect of additions of mPEG on the proteolytic activities of Proteinase K and a PEG-conjugate thereof, measured as the temperature at which a sample loses 50% of its initial activity after one hour of incubation in the presence of 0.5% (w/v) SDS ("TI$_{50}$").

FIG. 11 summarizes the results of the experiments shown in FIG. 10 and additional studies of the same type. Samples of PK and PEG-PK were preincubated at various temperatures in the presence of SDS and various concentrations of free MPEG prior to assay for caseinolytic activity. From the best-fitting equations for a 5-parameter sigmoid curve, the temperature corresponding to 50% inactivation ($TI_{50}$) was calculated. These temperatures are plotted as a function of the concentration of free mPEG in the preincubation solutions in FIG. 11.

Maximal stabilization of both Proteinase K and the conjugate was achieved by the addition of at least 3 mg of free mPEG per mL of solution, but the conjugate was consistently more stable. The PEG content of the conjugate used in this experiment corresponds to 0.07 mg of PEG per mL of preincubation solution. From FIG. 11, it can be estimated that it would take about 35–40 times as much free mPEG to raise the temperature of inactivation of the unmodified enzyme to that of the conjugate. The present inventors recognize that the introduction of such high concentrations of free mPEG into an extraction process might interfere with subsequent processing of the extracted nucleic acids or disease-related prion proteins. On the other hand, based on our results, the addition of free PEG (particularly unreactive polymers like mPEG) to polymer-proteinase conjugates to stabilize proteinases against harsh environments appears to be advantageous in certain industrial processes.

Example 10

Rapid Identification of Disease-Related Prions in Specimens from Humans and Animals Biopsy specimens of normal animal brain tissue and brain tissue from patients or animals with spongiform encephalopathies are homogenized in phosphate-buffered saline (pH 7.4) and portions are mixed with 100 micro-grams/mL of either Proteinase K or Proteinase K to which PEG has been coupled as described in Example 2. The samples are then incubated for 2 hours at 37° C. or for 15 minutes at a temperature between 50° C. and 65° C., before they are analyzed by SDS-PAGE and Western blot analysis with an anti-prion antiserum. An alternative method of analysis involves the use of an ELISA method. Protease-resistant, disease-related prion proteins with a molecular weight of approximately 30 kDa are seen in the specimens from patients or animals with spongiform encephalopathies after two hours of incubation at 37° C. with Proteinase K or with the PEG conjugates of Proteinase K. On the other hand, when the samples are incubated for 15 minutes at 50–65° C., only those samples containing the PEG conjugates of Proteinase K are digested sufficiently to permit the identification of the disease-related prions. By incorporating effective concentrations of guanidinium hydrochloride, guanidinium thiocyanate or urea into the digestion mixtures, the selective digestion of the protease-sensitive (non-disease-related) prions and other proteins by the conjugates of this invention are performed even more rapidly. Thus, the use of PEG-conjugated Proteinase K permits the molecular diagnosis of disease-related prion proteins to be adapted to high throughput screening methods. These methods are also applicable to white blood cells, lymph nodes and other tissues that are more accessible than biopsy specimens from the brain.

This invention is described with reference to certain embodiments thereof. The methods of this invention are similarly applicable to other types of proteinases and to other conjugation reagents. Therefore, the scope of this invention is not limited to the embodiments described, but is limited only by the scope of the claims. Workers of ordinary skill in the art can readily appreciate that other embodiments can be practiced without departing from the scope of this invention. All such variations are considered to be part of this invention.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for increasing the stability of Proteinase K, comprising contacting an initial Proteinase K with an amine-reactive poly(alkylene oxide) (PAO) having a molecular weight in the range of about 1 kDa to about 20 kDa to produce a covalent PAO-Proteinase K conjugate, wherein the number of amine-reactive PAO molecules coupled to said Proteinase K is three to seven PAO strands per said initial Proteinase K, wherein said conjugate has an integrated enzymatic activity that is greater than the integrated enzymatic activity of the initial proteinase after exposure to a temperature of about 30° C. to about 70° C. over a period of time of about one hour to about 18 hours.

2. The method of claim 1, wherein said amine-reactive poly(alkylene oxide) is selected from the group consisting of poly(ethylene oxide) (PEO), poly(ethylene glycol) (PEG), branched PEG, star-PEG, branched PEO, star-PEO, poly(propylene glycol) (PPG), copolymers of PEG and PPG, copolymers of PEO and PPG and poly(oxyethylene-oxymethylene) copolymers.

3. The method of claim 2, wherein said amine-reactive PAO is PEG or PEG.

4. The method of claim 1, wherein said PAO has a molecular weight in the range of about 2 kDa to about 5 kDa.

5. The method of claim 1, wherein said amine-reactive PAO forms a covalent bond with a lysine residue of said Proteinase K.

6. The method of claim 1, wherein said amine-reactive PAO forms a covalent bond with an amino-terminal residue of said Proteinase K.

7. The method of claim 1, wherein said polymer-proteinase conjugate is present in a composition further comprising an unreactive polymer.

8. The method of claim 7, wherein said unreactive polymer is present in said composition at a concentration of from about 1 mg/mL to about 100 mg/mL.

9. A polymer-proteinase conjugate prepared by conjugating an initial Proteinase K to an amine-reactive poly(alkylene oxide) (PAO) having a molecular weight in the range of about 1 kDa to about 20 kDA, comprising an initial Proteinase K covalentiy linked to three to seven polymer strands per molecule of said initial Proteinase K, said conjugate having integrated enzymatic activity at a temperature of about 50° C. that is greater than the integrated enzymatic activity of said initial Proteinase K proteinase under comparable conditions.

10. The conjugate of claim 9, wherein said poly(alkylene oxide) is selected from the group consisting of poly(ethylene oxide) (PEO), poly(ethylene glycol) (PEG), branched PEG, star PEG, branched PEO, star-PEO, poly(propylene glycol) (PPG), copolymers of PEG and PPG, copolymers of PEO and PPG and poly(oxyethylene-oxymethylene) copolymers.

11. The conjugate of claim 10, wherein said poly(alkylene oxide) is PEG or PEO.

12. The conjugate of claim 9, wherein said polymer has a molecular weight in the range of about 2 kDa to about 5 kDa.

13. The conjugate of claim 9, wherein said amine-reactive PAO is covalently linked to a lysine residue of said Proteinase K.

14. The conjugate of claim 9, wherein said conjugate comprises a plurality of PAO strands, each covalently linked to a lysine residue of said Proteinase K.

15. The conjugate of claim 9, wherein said amine-reactive PAO is covalently linked to an amino-terminal residue of said Proteinase K.

16. A conjugate, comprising an initial Proteinase K covalently attached to three to seven poly(alkylene oxide) (PAO) strands per molecule of said initial Proteinase K, wherein each strand of said PAO has a molecular weight in the range of about 1 kDa to about 20 kDa said conjugate having an integrated enzymatic activity over a period of 90 minutes at a temperature of about 50° C. in a solution of a chaotropic agent that is at least about 150% of the integrated enzymatic activity of said initial Proteinase K under comparable conditions.

17. The conjugate of claim 16, wherein said chaotropic agent is selected from the group consisting of sodium lauryl sulfate, sodium dodecyl sulfate (SDS), lithium dodecyl sulfate, urea and guanidinium salts.

18. The conjugate of claim 17, wherein said guanidinium salt is guanidine thiocyanate.

19. The conjugate of claim 17, wherein said chaotropic agent is 0.5% SDS.

20. The conjugate of claim 17, wherein said chaotropic agent is 2–4 M urea.

21. The conjugate of claim 16, wherein said poly(alkylene oxide) is selected from the group consisting of poly(ethylene oxide) (PEO), poly(ethylene glycol) (PEG), branched PEG, star-PEG, branched PEO, star-PEO, poly(propylene glycol) (PPG), copolymers of PEG and PPG, copolymers of PEO and PPG and poly(oxyethylene-oxymethylene) copolymers.

22. The conjugate of claim 21, wherein said PAO is PEG or PEO.

23. A conjugate comprising an initial Proteinase K covalently attached to three to seven poly(alkylene oxide) (PAO) strands per molecule of said initial Protemase K, wherein each PAO strand has a molecular weight in the range of 1 kDa to 20 kDa, said conjugate having integrated enzymatic activity after being heated for one hour at a temperature of about 50° C. in a solution containing 0.5 M guanidine thiocyanate that is at least four times that of said initial Proteinase K under comparable conditions.

24. The conjugate of claim 23, wherein poly(alkylene oxide) is selected from the group consisting of poly(ethylene oxide) (PEO), poly(ethylene glycol) (PEG), branched PEG, star-PEG, branched PEO, star-PEO, poly(propylene glycol) (PPG), copolymers of PEG and PPG, copolymers of PEO and PPG and poly(oxyethylene-oxymethylene) copolymers.

25. The conjugate of claim 11, wherein said PAO is PEG or PEO.

26. A method for increasing the stability of Proteinase K, comprising reacting an initial Proteinase K with an amine-reactive poly(alkylene oxide) (PAO) to produce a covalent PAO-Proteinase K conjugate that has an integrated enzymatic activity at a temperature of about 50° C. that is greater than at least about 150% of the integrated enzymatic activity of the initial proteinase, wherein each PAO strand has a molecular weight in the range of 1 kDa to 20 kDa, and the number of amine-reactive PAO molecules coupled to said proteinase is from 3 to 7.

27. The method of claim 26, wherein said amine-reactive poly(alkylene oxide) is selected from the group consisting of poly(ethylene oxide) (PEO), poly(ethylene glycol) (PEG), branched PEG, star-PEG, branched PEO, star-PEO, poly(propylene glycol) (PPG), copolymers of PEG and PPG, copolymers of PEO and PPG and poly(oxyethylene-oxymethylene) copolymers.

28. The method of claim 27, wherein said amine-reactive PAO comprises PEG or PEO.

29. A polymer-proteinase conjugate, comprising an initial Proteinase K covalently linked to three to seven poly(alkylene oxide) (PAO) strands per molecule of said initial Proteinase K, wherein each PAO strand has a molecular weight in the range of 1 kDa to 20 kDa, said conjugate having integrated enzymatic activity in a solution containing 0.5% SDS, 0.1 M GdnSCN or 2–4M urea at a temperature of about 50° C. that is greater than at least about 150% of the integrated enzymatic activity of said initial proteinase under comparable conditions.

30. The conjugate of claim 29, wherein said poly(alkylene oxide) is selected from the group consisting of poly(ethylene oxide) (PEO), poly(ethylene glycol) (PEG), branched PEG, star-PEG, branched PEO, star-PEO, poly(propylene glycol) (PPG), copolymers of PEG and PPG, copolymers of PEO and PPG and poly(oxyethylene-oxymethylene) copolymers.

31. The conjugate of claim 30, wherein said PAO is PEG or PEO.

32. The conjugate of claim 29, wherein the integrated enzymatic activity of said conjugate is about or greater than 2 times the integrated enzymatic activity of said initial Proteinase K.

33. The conjugate of claim 29, wherein the integrated enzymatic activity of said conjugate is about or greater than 3 times the integrated enzymatic activity of said Proteinase K.

34. The conjugate of claim 29, wherein the integrated enzymatic activity of said conjugate is about or greater than 5 times the integrated enzymatic activity of said initial Proteinase K.

35. The conjugate of claim 29, wherein the integrated enzymatic activity of said conjugate is about or greater than 7 times the integrated enzymatic activity of said initial Proteinase K.

36. A polymer-protemase conjugate, comprising an initial Proteinase K covalently linked to three to seven strands of PEG per molecule of said initial Proteinase K, wherein each strand of PEG has a molecular weight in the range of about 1 kDa to about 20 kDa, said conjugate having an integrated enzymatic activity at a temperature of about 50° C. that is greater than at least about 150% of the integrated enzymatic activity of said initial Proteinase K under comparable conditions.

37. The conjugate of claim 36, wherein said at least one strands of PEG is attached to at least one lysine residue of said initial Proteinase K.

38. The conjugate of claim 36 having three strands of PEG.

39. The conjugate of claim 36 having four strands of PEG.

40. The conjugate of claim 36 having five strands of PEG.

41. The conjugate of claim 36 having six strands of PEG.

42. The conjugate of claim 36 having seven strands of PEG.

* * * * *